United States Patent [19]
Bergh et al.

[11] Patent Number: 5,272,066
[45] Date of Patent: Dec. 21, 1993

[54] SYNTHETIC METHOD FOR ENHANCING GLYCOPROTEIN STABILITY

[75] Inventors: Michel L. E. Bergh; S. Catherine Hubbard, both of Somerville, Mass.; James R. Rasmussen, Ithaca, N.Y.

[73] Assignee: Massachusetts Institute of Technology, Cambridge, Mass.

[21] Appl. No.: 785,913

[22] Filed: Nov. 4, 1991

Related U.S. Application Data

[60] Continuation of Ser. No. 337,294, Mar. 13, 1989, abandoned, which is a division of Ser. No. 837,604, Mar. 7, 1986, Pat. No. 4,925,796.

[51] Int. Cl.$^5$ .................. C12P 19/18; C12P 19/26; C12P 19/28; C12P 21/00; C12P 21/06; C12Q 1/00
[52] U.S. Cl. .................. 435/97; 435/84; 435/85; 435/68.1; 435/69.51; 435/7.6
[58] Field of Search .................. 435/7, 68.1, 69, 69.51, 435/7.6, 84, 85, 97

[56] References Cited

U.S. PATENT DOCUMENTS 4,184,917  1/1980  Dorner et al. .................. 435/68
4,770,994  9/1988  Rittenhouse .................. 435/7

OTHER PUBLICATIONS

Zeffren & Hall (1973) Ch. 3, pp. 33-52, John Wiley & Sons, New York.
Stowell & Lee (1982) *Meth Enzymol*, 83, pp. 278-288.
Yan & Wold (1984) *Biochemistry*, 23, pp. 3759-3765.
Schachter et al "The Biochemistry of Glycoproteins and Proteoglycans", pp. 85-111, W. Lennarz, ed., Plenum, N.Y.
Berger, et al., *Experientia* 48(10), 1129-1258 (1982).
Fuhrmann, et al., *Biochimica at Biophysica Acta* 825, 95-110 (1985).
Chu, *J. Biol. Chem.* 261, 172-177 (1986).
Kalyan, et al., *J. Biol. Chem.* 258(1), 67-74 (1983).
Schwarz, et al., *Adv. Carbohydrate Chem. Biochem.* 40, 312-314, 321-322, 348-353 (1982).
Hubbard, S. C., et al., *Ann. Rev. Biochem.*, 50, 555-583 (1981).
Kornfeld, R., et al., *Ann. Rev. Biochem.* 54, 631-664 (1985).
Trimble, R. B., et al., *Anal. Biochem.*, 141, 515-522 (1984).
Lee, Y. C., *J. Biol. Chem.* 258, 199-202 (1983).
Baynes, J. W., et al., *J. Biol. Chem.* 251, 6016-6024 (1976).
Weinstein, J., et al., *J. Biol. Chem.* 257, 13845-13853 (1982).
Higa, H. H., et al., *J. Biol. Chem.* 260, 8838-8847 (1985).
Hickman, *J. Biol. Chem.* 245, 759-766 (1970).

(List continued on next page.)

*Primary Examiner*—David M. Naff
*Assistant Examiner*—Jon Weber
*Attorney, Agent, or Firm*—Kilpatrick & Cody

[57] ABSTRACT

A method for modifying eukaryotic and prokaryotic proteins to extend their in vivo circulatory lifetimes. In the preferred embodiment, enzymatic and/or chemical treatments are used to produce a modified protein carrying one or more covalently attached trisaccharide, sialic acid→galactose→N-acetylglucosamine→(SA→Gal→GlcNAc→), or tetrasaccharide (SA→Gal→GlcNAc→GlcNAc→) moieties. The method can be applied to any natural or recombinant protein possessing asparagine-linked oligosaccharides or to any non-glycosylated protein that can be chemically or enzymatically derivatized with the appropriate carbohydrate units. Following injection into an animal, the modified glycoproteins are protected from premature clearance by cells of the liver and reticulo-endothelial system which recognize and rapidly internalize circulating glycoproteins with carbohydrate chains containing terminal Gal, GlcNAc, fucose or mannose residues. The method can also be used to mask antigenic determinants on foreign proteins which would otherwise produce an immune response or to "target" a protein for recognition by sugarspecific cell surface receptors.

13 Claims, 7 Drawing Sheets

OTHER PUBLICATIONS

Elting, J. J., et al., *Methods in Enzymology* 83, 408–415 (Academic Press, NY (1982)).

Tabas, I., et al., *Methods in Enzymology*, 83, 416–429 (Academic Press 1982).

Tai, T., et al., *Biochem. Biophys. Res. Com.* 78(1), 434–441 (1977).

Tarentino, A. L., et al., *Methods in Enzymology* 50, 574–580 (Academic Press 1978).

Muramatsu, T., *Methods in Enzymology* 50, 555–559 (Academic Press, NY 1978).

Kobata, A., *Methods in Enzymology* 50, 567–574 (Academic Press, NY 1978).

Sharon, N., et a., *C&EN*, pp. 21–44 (Mar. 30, 1981).

Snider, M. D., "Biosynthesis of Glycoproteins: Formation of N-Linked Oligosaccharides".

Sharon, N., *TIBS.* 9 (1984).

Hughes, R. C., *Glycoproteins* pp. 36–57 (W. J. Brammer and M. Edidin, Editors) (Chapman and Hall, NY).

Neufeld, et al., *The Biochemistry of Glycoproteins and Proteoglycans* pp. 241–265 (W. J. Lennarz, Editor) (Plenum Press, NY).

Olden, K., et al., *TIBS* 78–82 (Feb. 1985).

Feizi, T., et al, *TIBS* 24–29 (Jan. 1985).

5,272,066

SYNTHETIC METHOD FOR ENHANCING GLYCOPROTEIN STABILITY

The United States Government has certain rights in this invention by virtue of National Institutes of Health grants No. CA26712, GN31318, and CA14051.

This which is a continuation of U.S. Ser. No. 07/337,294, filed Mar. 13, 1989, now abandoned, and is a divisional of U.S. Ser. No. 06/837,604, entitled "Method for Enhancing Glycoprotein Stability" filed Mar. 7, 1986, by Michel L. E. Bergh, S. Catherine Hubbard, and James R. Rasmussen issued May 15, 1990 as U.S. Pat. No. 4,925,796.

BACKGROUND OF THE INVENTION

Glycoproteins, Proteins with covalently bound sugars, are found in plants, animals, insects, and even many unicellular eukaryotes such as yeast. They occur within cells in both soluble and membrane-bound forms, in the intercellular matrix, and in extracellular fluids. The carbohydrate moieties of these glycoproteins can participate directly in the biological activity of the glycoproteins in a variety of ways: protection from proteolytic degradation, stabilization of protein conformation, and mediation of inter- and intracellular recognition. Examples of glycoproteins include enzymes, serum proteins such as imunoglobulins and blood clotting factors, cell surface receptors for growth factors and infectious agents, hormones, toxins, lectins and structural proteins.

Natural and recombinant proteins are being used as therapeutic agents in humans and animals. In many cases a therapeutic protein will be most efficacious if it has an appreciable circulatory life-time. At least four general mechanisms can contribute to a shortened circulatory lifetime for an exogenous protein: proteolytic degradation, clearance by the imune system if the protein is antigenic or immunogenic, clearance by cells of the liver or reticulo-endothelial system that recognize specific exposed sugar units on a glycoprotein, and clearance through the glomerular basement membrane of the kidney if the protein is of low molecular weight. The oligosaccharides of a glycoprotein can exert a strong effect on the first three of these clearance mechanisms.

The oligosaccharide chains of glycoproteins are attached to the polypeptide backbone by either N- or O-glycosidic linkages. In the case of N-linked glycans, there is an amide bond connecting the anomeric carbon (C-1) of a reducing-terminal N-acetylglucosamine (GlcNAc) residue of the oligosaccharide and a nitrogen of an asparagine (Asn) residue of the polypeptide. In animal cells, O-linked glycans are attached via a glycosidic bond between N-acetylgalactosamine (GalNAc), galactose (Gal), or xylose and one of several hydroxyamino acids, most commonly serine (Ser) or threonine (Thr), but also hydroxyproline or hydroxylysine in some cases. The O-linked glycans in the yeast *Saccharomyces cerevisiae* are also attached to serine or threonine residues, but, unlike the glycans of animals, they consist of one to several α-linked mannose (Man) residues. Mannose residues have not been found in the O-linked oligosaccharides of animal cells.

The biosynthetic pathways of N- and O-linked oligosaccharides are quite different. O-Linked glycan synthesis is relatively simple, consisting of a step-by-step transfer of single sugar residues from nucleotide sugars by a series of specific glycosyltransferases. The nucleotide sugars which function as the monosaccharide donors are uridine-diphospho-GalNAc (UDP-GalNAc), UDP-GlcNAc, UDP-Gal, guanidinediphospho-fucose (GDP-Fuc), and cytidine-monophospho-sialic acid (CMP-SA). N-Linked oligosaccharide synthesis, which is much more complex, is described below.

The initial steps in the biosynthesis of N-linked glycans have been preserved with little change through evolution from the level of unicellular eukaryotes such as yeast to higher plants.,and man. For all of these organisms, initiation of N-linked oligosaccharide assembly does not occur directly on the Asn residues of the protein, but rather involves preassembly of a lipid-linked precursor oligosaccharide which is then transferred to the protein during or very soon after its translation from MRNA. This precursor oligosaccharide, which has the composition $Glc_3Man_9GlcNAc_2$ and the structure shown in FIG. 1A, is synthesized while attached via a pyrophosphate bridge to a polyisoprenoid carrier lipid, a dolichol. This assembly is a complex process involving at least six distinct membrane-bound glycosyltransferases. Some of these enzymes transfer monosaccharides from nucleotide sugars, while others utilize dolichol-linked monosaccharides as sugar donors. After assembly of the lipid-linked precursor is complete, another membrane-bound enzyme transfers it to sterically accessible Asn residues which occur as part of the sequence -Asn-X-Ser/Thr-. The requirement for steric accessibility is presumably responsible for the observation that denaturation is usually required for in vitro transfer of precursor oligosaccharide to exogenous proteins.

Glycosylated Asn residues of newly-synthesized glycoproteins transiently carry only one type of oligosaccharide, $Glc_3Man_9GlcNAc_2$. Modification, or "processing," of this structure generates the great diversity of structures found on mature glycoproteins, and it is the variation in the type or extent of this processing which accounts for the observation that different cell types often glycosylate even the same polypeptide differently.

The processing of N-linked oligosaccharides is accomplished by the sequential action of a number of membrane-bound enzymes and begins immediately after transfer of the precursor oligosaccharide $Glc_3Man_9GlcNAc_2$ to the protein. In broad terms, N-linked oligosaccharide processing can be divided into three stages: removal of the three glucose residues, removal of a variable number of mannose residues, and addition of various sugar residues to the resulting trimmed "core," i.e., the $Man_3GlcNAc_2$ portion of the original oligosaccharide closest to the polypeptide backbone. A simplified outline of the processing pathway is shown in FIG. 2.

Like the assembly of the precursor oligosaccharide, the removal of the glucose residues in the first stage of processing has been preserved through evolution. In yeast and in vertebrates, all three glucose residues are trimmed to generate N-linked $Man_9GlcNAc_2$. Processing sometimes stops with this structure, but usually it continues to the second stage with removal of mannose residues. Here the pathway for yeast diverges from that in vertebrate cells.

As shown in FIG. 1B, four of the mannose residues of the $Man_9GlcNAc_2$ moiety are bound by $\alpha 1 \rightarrow 2$ linkages. By convention the arrow points toward the reducing terminus of an oligosaccharide, or in this case, toward the protein-bound end of the glycan; α or β indicate the anomeric configuration of the glycosidic bond; and the two numbers indicate which carbon atoms on each monosaccharide are involved in the bond. The four α1→2-linked mannose residues can be removed by Mannosidase I to generate N-linked $Man_{5-8}GlcNAc_2$, all of which are commonly found on vertebrate glycoproteins. Oligosaccharides with the composition $Man_{5-9}GlcNAc_2$ are said to be of the "high-mannose" type.

As shown in FIG. 2, protein-linked $Man_5GlcNAc_2$ (Structure M-c) can serve as a substrate for GlcNAc transferase I, which transfers a β1→2-linked GlcNAc residue from UDP-GlcNAc to the α1→3-linked mannose residue to form $GlcNAcMan_5GlcNAc_2$ (Structure M-d). Mannosidase II can then complete the trimming phase of the processing pathway by removing two mannose residues to generate a protein-linked oligosaccharide with the composition $GlcNAcMan_3GlcNAc_2$ (Structure M-e). This structure is a substrate for GlcNAc transferase II, which can transfer a β1→2-linked GlcNAc residue to the α1→6-linked mannose residue (not shown).

It is at this stage that the true complexity of the processing pathway begins to unfold. Simply stated, monosaccharides are sequentially added to the growing oligosaccharide chain by a series of membrane-bound Golgi glycosyltransferases, each of which is highly specific with respect to the acceptor oligosaccharide, the donor sugar, and the type of linkage formed between the sugars. Each type of cell has an extensive but discrete set of these glycosyltransferases. These can include at least four more distinct GlcNAc transferases (producing β1→3, β1→4, or β1→6 linkages); three galactosyltransferases (producing β1→4, β1→3, and β1→3 linkages); two sialyltransferases (one producing α2→3 and another, α2→6 linkages); three fucosyltransferases (producing α1→2, α1→3, α1→4 or α1→6 linkages); and a growing list of other enzymes responsible for a variety of unusual linkages. The cooperative action of these glycosyltransferases produces a diverse family of structures collectively referred to as "complex" oligosaccharides. These may contain two (for example, Structure M-f in FIG. 2), three (for example, FIG. 1C or Structure M-g in FIG. 2), or four outer branches attached to the invariant core pentasaccharide, $Man_3GlcNAc_2$. These structures are referred to in terms of the number of their outer branches: biantennary (two branches), triantennary (three branches) or tetraantennary (four branches). The size of these complex glycans varies from a hexasaccharide (on rhodopsin) to very large polylactosaminylglycans, which contain one or more outer branches with repeating ($Galβ1→4GlcNAcβ1→3$) units (on several cell surface glycoproteins such as the erythrocyte glycoprotein Band 3 and the macrophage antigen Mac-2). Despite this diversity, the specificities of the glycosyltransferases do produce some frequently recurring structures. For example, the outer branches of many complex N-linked oligosaccharides consist of all or part of the sequence

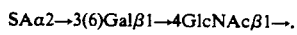

$SAα2→3(6)Galβ1→4GlcNAcβ1→$.

One or two of these trisaccharide moieties may be attached to each of the two α-linked mannose residues of the core pentasaccharide, as in Structures M-f and M-g of FIG. 2.

Unlike transcription of DNA or translation of MRNA, which are highly reproducible events, oligosaccharide biosynthesis does not take place on a template. As a consequence, considerable heterogeneity is usually observed in the oligosaccharide structures of every glycoprotein. The differences are most commonly due to variations in the extent of processing. The single glycosylation site of the chicken egg glycoprotein ovaybumin, for example, contains a structurally related "family" of at least 18 different oligosaccharides, the great majority of which are of the high-mannose or related "hybrid" type (for example, Structure M-h in FIG. 2). Many glycoproteins contain multiple glycosylated Asn residues, and each of these may carry a distinct family, of oligosaccharides. For example, one site may carry predominantly high-mannose glycans, another may carry mostly fucosylated biantennary complex chains, and a third may carry fucose-free tri- and tetraantennary complex structures. Again, all of these glycans will contain the invariant $Man_3GlcNAc_2$ core.

As discussed above, the initial stages of N-linked oligosaccharide synthesis in the yeast Saccharomyces cerevisiae closely resemble those occurring in vertebrate cells. As in higher organisms, lipid-linked $Glc_3Man_9GlcNAc_2$ is assembled, its oligosaccharide chain transferred to acceptor Asn residues of proteins, and its three glucose residues are removed soon after transfer. Yeast cells can remove only a single mannose residue, however, so that the smallest and least-processed N-linked glycans have the composition $Man_{8-9}GlcNAc_2$. Processing can stop at this stage or continue with the addition of as many as 50 or more α-linked mannose residues to $Man_9GlcNAc_2$ (FIG. 2, Structure Y-c) to generate a mannan (for example, Structure Y-d). Just as glycoproteins in maninalian-cells may hive predominantly high-mannose oligosaccharides at one glycosylated Asn residue and highly processed complex glycans at another, yeast glycoproteins such a% external invertase commonly have some glycosylation sites with $Man_{8-9}GlcNAc_2$ chains, while other sites carry mannans.

Unlike eukaryotic cells, bacteria lack the enzymatic machinery to assemble lipid-linked $Glc_3Man_9GlcNAc_2$ or transfer it to proteins. Thus, although proteins synthesized in E. coli contain many -Asn-X-Ser/Thr- sequences, they are not glycosylated.

From the foregoing discussion, it is apparent that the glycosylation status of a glycoprotein will depend on the cell in which it is produced. The glycans of a protein synthesized in cultured mammalian cells will resemble those of the same protein isolated from a natural animal source such as a tissue but are unlikely to be identical. Proteins glycosylated by yeast contain high-mannose oligosaccharides and mannans, and proteins synthesized in a bacterium such as E. coli will not be glycosylated because the necessary enzymes are absent.

The precise composition and structure of the carbohydrate chain(s) on a glycoprotein can directly influence its serum lifetime, since cells in the liver and reticulo-endothelial system can bind and internalize circulating glycoproteins with specific carbohydrates. Hepatocytes have receptors on their surfaces that recognize oligosaccharide chains with terminal (i.e., at the outermost end(s) of glycans relative to the polypeptide) Gal residues, macrophages contain receptors for terminal Man or GlcNAc residues, and hepatocytes and lymphocytes have receptors for exposed fucose residues. No sialic acid-specific receptors have been found, however. Although somewhat dependent on the spatial arrangement of the oligosaccharides, as a general rule, the greater the number of exposed sugar residues recognized by cell surface receptors in the liver and reticuloendothelial system, the more rapidly a glycoprotein will be cleared from the serum. Because of the absence of sialic acid-specific receptors, however, oligosaccharides with all branches terminated, or "capped," with sialic acid will not promote the clearance of the protein to which they are attached.

The presence and nature of the oligosaccharide chain(s) on a glycoprotein can also affect important biochemical properties in addition to its recognition by sugar-specific receptors on liver and reticulo-endothelial cells. Removal of the carbohydrate from a glycoprotein will usually decrease its solubility, and it may also increase its susceptibility to proteolytic degradation by destabilizing the correct polypeptide folding pattern and/or unmasking protease-sensitive sites. For similar reasons, the glycosylation status of a protein can affect its recognition by the immune system.

It is therefore an objective of the present invention to provide a method for modifying oligosaccharide chains of glycoproteins isolated from natural sources or produced from recombinant DNA in yeast, insect, plant or vertebrate cells in a manner that increases serum lifetime or targets the protein to specific cell types.

It is another objective of the invention to provide an in vitro method for glycosylating proteins produced from bacterial, yeast, plant, viral or animal DNA in a manner that enhances stability and effective biological activity.

It is a further objective of the invention to provide a method for glycosylation of proteins or modification of oligosaccharide chains on glycoproteins which is efficient, reproducible and cost-effective.

SUMMARY OF THE INVENTION

A method for modifying eukaryotic and prokaryotic proteins to extend their in vivo circulatory lifetimes or to control their site of cellular uptake in the body. In preferred embodiments, enzymatic and/or chemical treatments are used to produce a modified protein carrying one or more covalently attached trisaccharide

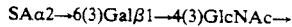

or tetrasaccharide.

moieties. In alternative embodiments, one or two GlcNAc$_2$ residues bound to the protein are used as a basis for construction of other oligosaccharides by elongation with the appropriate glycosyltransferases. The method can be applied to any natural or recombinant protein possessing Asn-linked oligosaccharides or to any non-glycosylated protein that can be chemically or enzymatically derivatized with the appropriate carbohydrate residues.

Generation of glycoproteins containing Asn-linked

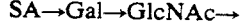

The preferred oligosaccharide modification scheme consists of the following steps wherein all but the-Asn-linked GlcNAc$_2$ of the N-linked oligosaccharide chains are enzymatically or chemically removed from the protein and a trisaccharide constructed in its place:

Step 1. Generation of GlcNAc→Asn(protein). The initial step is cleavage of the glycosidic bond connecting the two innermost core GlcNAc residues of some or all N-linked oligosaccharide chains of a glycoprotein with an appropriate endo-β-N-acetylglucosaminidase such as Endo H or Endo F. Endo H cleaves the high-mannose and hybrid oligosaccharide chains of glycoproteins produced in eukaryotic cells as well as the mannans produced in yeast such as *Saccharomyces cerevisiae*, removing all but a single GlcNAc$_2$ residue attached to each glycosylated Asn residue of the polypeptide backbone. Endo F can cleave both high-mannose and biantennary complex chains of N-linked oligosaccharides, again leaving a single GlcNAc$_2$ residue attached at each glycosylation site. If a given glycoprotein contains complex oligosaccharides such as tri- or tetraantennary chains which are inefficiently cleaved by known endoglycosidases, these chains can be trimmed with exoglycosidases such as sialidase, β- and α-galactosidase, α-fucosidase and β-hexosaminidase. The innermost GlcNAc$_2$ residue of the resulting core can be then be exposed by any of several procedures. One procedure is digestion with Endo F or other endo-β-N-acetylglucosaminidases such as Endo D. A second procedure is digestion with α-mannosidase followed by digestion with either Endo L or with β-mannosidase and β-hexosaminidase.

Alternatively, glycoproteins normally bearing complex Asn-linked oligosaccharides can be produced in mammalian cell culture in the presence of a processing inhibitor such as swainsonine or deoxymannojirimycin. The resulting glycoprotein will bear hybrid or high-mannose chains susceptible to cleavage by Endo H, thereby eliminating the need for an initial treatment of the glycoprotein with exoglycosidases. In a related variation, the glycoprotein may be produced in a mutant cell line that is incapable of synthesizing complex N-linked chains resistant to endoglycosidases such as Endo H or Endo F.

All sugars other than the N-linked GlcNAc$_2$ residues may also be removed chemically rather than enzymatically by treatment with trifluoromethanesulfonic acid or hydrofluoric acid. In general, chemical cleavage can be expected to be less useful than enzymatic methods because of the denaturing effects of the relatively harsh conditions used.

Step 2. Attachment of Gal to GlcNAc→Asn(protein). The second step is the enzymatic addition of a Gal residue to the residual GlcNAc on the protein by the action of a galactosyltransferase. The preferred galactosyltransferase is a bovine milk enzyme which transfers Gal to GlcNAc in the presence of the sugar donor UDP-Gal to form a β1→4 linkage. In another variation, galactose can be added to the GlcNAc residue with a β1→3 linkage by the use of a galactosyltransferase from a source such as pig trachea.

Step 3. Attachment of SA to Gal→GlcNAc→Asn(protein). The final step is the enzymatic addition of a sialic acid residue to Galβ1→4(3)GlcNAc→Asn(protein). This reaction can be carried out with an α2→6-sialyltransferase isolated, for example, from bovine colostrum or rat liver, which transfers SA from CMP-SA to form an α2→6 linkage to the terminal galactose residue of Galα1→4(3 )-GlcNAc→Asn(protein). Alternatively, an α2→3-sialyltransferase may be used to form an α2→3 linkage to each terminal Gal residue. Although the preferred sialic acid is N-acetylneuraminic acid (NeuAc), any naturally occurring or chemically synthesized sialic acid which the sialyltransferase can transfer from the CPM-SA derivative to galactose may be used, for example, N-glycolyl neuraminic acid, 9-0-acetyl-N-acetyl neuraminic acid, and 4-0-acetyl-N-acetyl neuraminic acid.

Generation of glycoproteins containing Asn-linked SA→Gal→GlcNAc→GlcNAc→

In a second embodiment, the oligosaccharide chains of the glycoprotein, whether natural or produced in the presence of a processing inhibitor or in a mutant cell line, are trimmed back to the two, rather than one, innermost core GlcNAc$_2$ residues by the use of appropriate exoglycosidases. For example, α and β-mannosidase would be used to trim a high-mannose oligosaccharide. The product of this treatment, GlcNAcβ1→4GlcNAc→Asn(protein), is then converted to the tetrasaccharide SAα2→6(3)Galβ→4(3)GlcNAcβ1→4GlcNAc→Asn-(protein) by sequential treatment with galactosyl- and sialyltransferases.

Attachment of oligosaccharides to non-glycosylated amino acid residues of proteins.

In a third embodiment, an oligosaccharide such as the trisaccharide SA→Gal→GlcNAc→ or disaccharide SA→Gal→ is attached at non-glycosylated amino acid residues of a protein expressed either in a eukarykotic system or in a bacterial system. For example, to attach the trisaccharide SA→Gal→GlcNAc, the protein is treated with a chemically reactive glycoside derivative of GlcNAc→, Gal→GlcNAc→, or SA→Gal→GlcNAc→. In the first two cases, the mono- or disaccharide is then extended to the trisaccharide by the appropriate glycosyltransferase(s). The initial carbohydrate moieties can be attached to the protein by a chemical reaction between a suitable amino acid and a glycoside derivative of the carbohydrate containing an appropriately activated chemical group. Depending on, the activation group present in the glycoside, the carbohydrate will be attached to amino acids with free amino groups, carboxyl groups, sulfhydryl groups, or hydroxyl groups or to aromatic amino acids.

Generation of other oligosaccharides by elongation of protein-linked GlcNAc residues.

Variations of the disclosed procedures can be used to produce glycoproteins with oligosaccharides other than the tri- or tetrasaccharides described above. For example, extended oligosaccharide chains consisting of

or

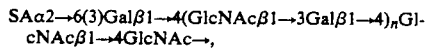

where n is 1-10, can be constructed by subjecting a glycoprotein carrying one or two core GlcNAc residues to alternate rounds of β1→4 galactosyltransferase and β1→3 N-acetylglucosaminyltransferase treatments. The resulting extended oligosaccharide chain can be useful for increasing solubility or masking protease-sensitive or antigenic sites of the polypeptide.

Many other useful oliciosaccharide structures can be constructed by elongation of protein-linked monosaccharides or disaccharides with the use of appropriate glycosyltransferases. An example is the branched fucosylated trisaccharide

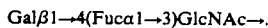

These and other structures could be useful in preferentially "targeting" a glycoprotein to a specific tissue known to contain receptors for a specific mono- or oligosaccharide.

DETAILED DESCRIPTION OF THE INVENTION

Figures 1A, 1B, 1C:
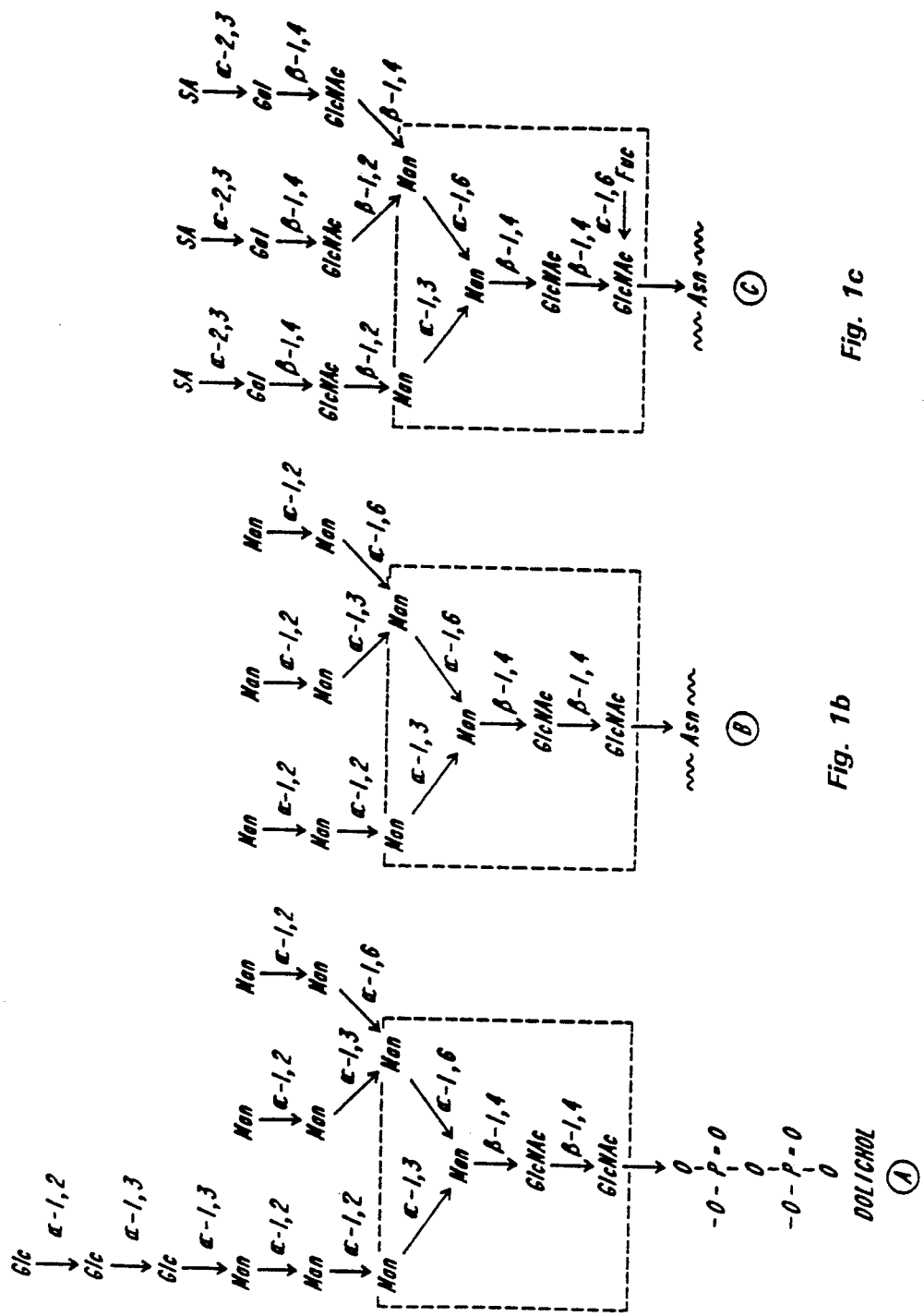
FIG. 1 shows the structures of (A), the lipid-linked precursor oligosaccharide, Glc$_3$Man$_9$GlcNAc$_2$; (B), a high-mannose Asn-linked oligosaccharide, Man$_9$GlcNAc$_2$; and (C), a typical triantennary complex Asn-linked oligosaccharide. The anomeric configurations and linkage positions of the sugar residues are indicated, and dotted lines enclose the invariant pentasaccharide core shared by all known eukaryotic Asn-linked oligosaccharides.

The present invention is a method for modifying proteins wherein oligosaccharide chains are bound to the protein to enhance in vivo stability or to target the protein to cells having specific receptors for an exposed saccharide in the attached oligosaccharide chain(s). The method has two principal embodiments. The first is to cleave the existing Asn-linked oligosaccharide chains on a glycoprotein to leave one or two GlcNAc residues attached to the protein at Asn and then enzymatically extend the terminal GlcNAc to attach Gal and SA. The second is to chemically or enzymatically attach a GlcNAc or Gal residue to the protein at any of a number of different amino acids and then enzymatically extend the terminal GlcNAc or Gal to form an oligosaccharide chain capped with sialic acid. There are a number of variations of the methods and enzymes used at each step of the methods, depending on the substrate and desired oligosaccharide structure.

A. Generation of glycoproteins containing SA→Gal→GlcNAc→Asn-(protein)

Step 1. Generation of GlcHAc→Asn(protein). There are several methods for preparing glycoproteins containing a single GlcNAc$_2$ residue attached to glycosylated asparagine residues. Six methods are as follows.

a. Cleavage by Endo H. To generate GlcNAc→Asn(-protein) enzymatically on glycoproteins having one or more oligosaccharides of the high-mannose or mannan type, the glycoprotein is incubated with an endo-β-N-acetylglucosaminidase capable of cleaving these oligosaccharide structures. The enzyme hydrolyzes the bond between the two core GlcNAc$_2$ residues of susceptible N-linked oligosaccharides, leaving behind a single GlcNAc$_2$ residue attached to the glycosylated Asn residues. The preferred enzyme for this purpose is Endo H, which has been isolated from *Streptomyces plicatus*. The enzyme is available either as the naturally occurring protein or as the recombinant DNA product expressed in *E. coli* or *Streptomyces lividans*.

Endo H cleaves all susceptible oligosaccharide structures of denatured glycoproteins and many of those on native glycoproteins. However, in native glycoproteins the GlcNAc$_2$ cores of some high-mannose glycans may be protected from cleavage by Endo H due to steric factors such as polypeptide folding. This can frequently be overcome by the use of one or several mild denaturing agents that promote partial polypeptide unfolding. Examples of such mild denaturants include detergent such as Triton X-100, NP-40, octyl glucoside, deoxy-cholate and dilute sodium dodecyl sulfate; disulfide bond reducing agents such as dithiothreitol and β-mercaptoethanol; chaotropic agents such as urea, guanidinium hydrochloride and sodium isothiocyanate; and low concentrations of organic solvents such as alcohols (methanol, ethanol, propanol or butanol), DMSO or acetone. Endo H is a very stable enzyme, active over a pH range of about 5 to 6.5, in low- or high-ionic strength buffers, and in the presence of the above-mentioned denaturing agents or protease inhibitors such as phenylmethanesulfonyl, fluoride, EDTA, aprotinin, leupeptide and pepstatin. Protocols for the use of Endo H have been published by Trimble and Maley in *Anal. Biochem.* 141, 515-522 (1984). The precise set of reaction conditions which will optimize the cleavage of oligosaccharides by Endo H while preserving biological activity will most likely vary depending on the glycoprotein being modified and can be determined routinely by someone of ordinary skill in this field.

In situations where one or more intact high-mannose glycans persist even after incubation under the most stringent Endo H reaction conditions judged safe to use, exposed mannose residues can be trimmed away by the use of an α-mannosidase such as the commercially available α-mannosidase from jack bean. While high-mannose oligosaccharides modified in this way will not serve as substrates for the further modification reactions described below, this treatment should reduce the possibility that mannose-specific receptors on macrophages or other cells might bind to residual high-mannose glycan(s) on the glycoprotein and cause its premature clearance from the circulation.

As mentioned earlier, yeast glycoproteins sometimes contain O-linked oligosaccharides consisting of one to four α-linked mannose residues. Because these could bind to a mannose-specific receptor and shorten the serum lifetime of a glycoprotein, it is advisable to treat any protein found to contain such oligosaccharides with an α-mannosidase such as the enzyme from jack bean. This would remove all but the innermost, protein-linked mannose residue from the O-linked chains. Because α-mannosidase treatment could interfere with subsequent cleavage by Endo H or Endo C$_{II}$, it should be performed after digestion with these enzymes.

Figure 2:
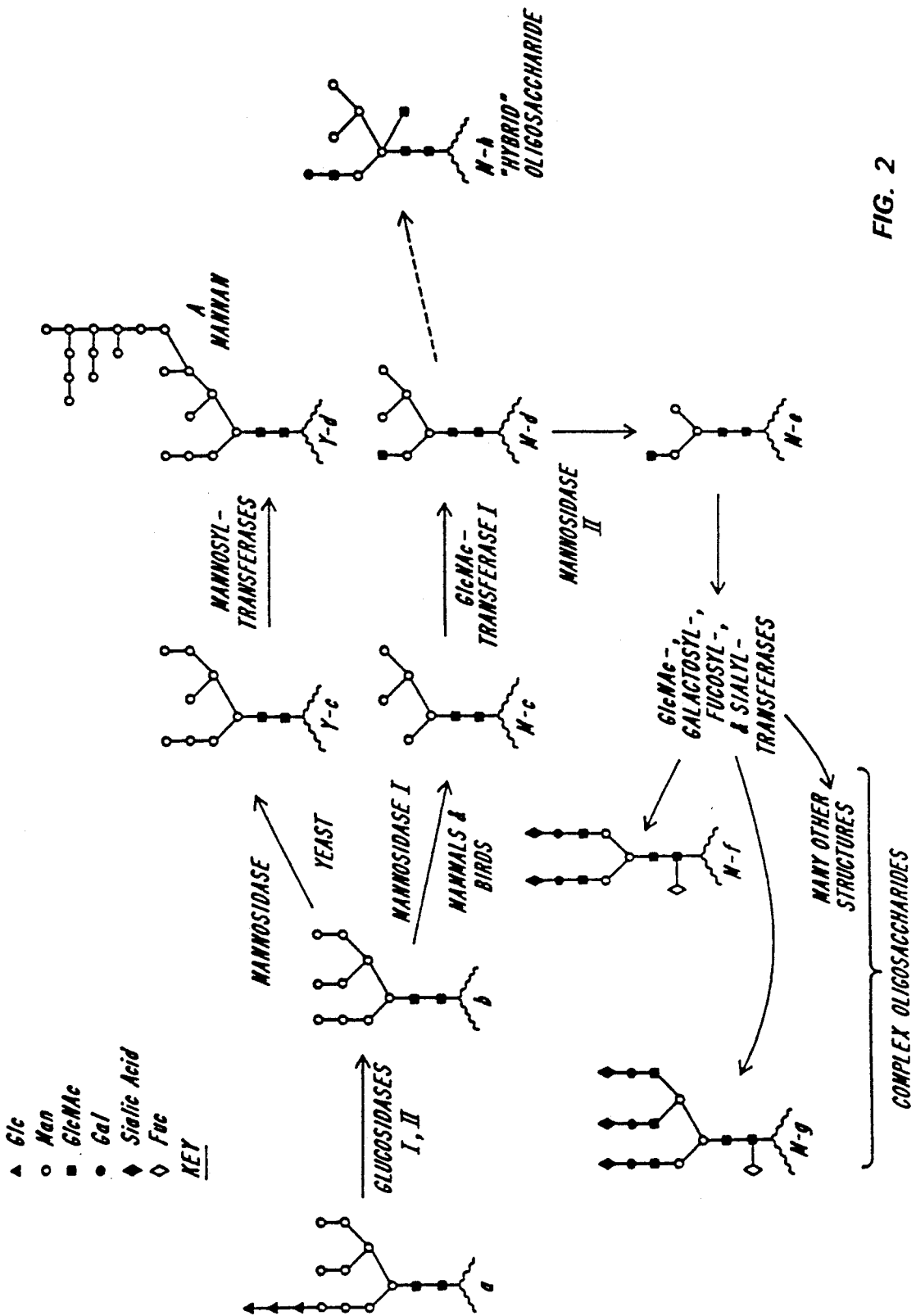
FIG. 2 is a simplified biosynthetic pathway for Asn-linked oligosaccharide biosynthesis in yeast and higher organisms. For clarity, anomeric configurations and linkage positions are not shown, but the arrangement of the branches is the same as in FIG. 1.

A common O-linked oligosaccharide in animal cells is Gal→GalNAc→Ser/Thr(protein). These glycans can be removed with the enzyme endo-α-N-acetylgalactosaminidase, which is commercially available from Genzyme Corp., Boston Mass. Many other mammalian O-linked oligosaccharides can be converted to Gal→GalNAc→Ser/Thr(protein) by treatment with exoglycosidases such as sialidase, β-hexosaminidase and α-fucosidase. The resulting protein-linked disaccharides could then be removed from the polypeptide with endo-α-N-acetylgalactosaminidase.

b. Cleavage by other endo-β-N-acetylglucosaminidases. Several other endo-β-N-acetylglucosaminidases are also capable of cleaving between the two innermost GlcNAc residues of various N-linked oligosaccharides. The oligosaccharide specificities of these enzymes vary and are summarized in Table I. Two of these endoglycosidases, Endo C$_{II}$ and Endo F, can be used in place of Endo H to cleave high-mannose glycans. Unlike Endo H, however, Endo F is also active with biantennary complex N-linked oligosaccharides. Although the N-linked oligosaccharides of vertebrates are not substrates for Endo D, this enzyme would be active with glycoproteins produced by insect cells, which produce significant quantities of N-linked Man$_3$GlcNAc$_2$ in addition to high-mannose oligosaccharides, as reported by Hsieh and Robbins in *J. Biol. Chem.* 259, 2375-82 (1984). In situations where the target glycoprotein contains multiple oligosaccharides sensitive to -different endo-β-N-acetylglucosaminidases, the glycoprotein can be incubated with the enzymes either sequentially or in combination to maximize cleavage.

c. Cleavage by Endo H after incubation of cultured cells with oligosaccharide processing inhibitors. Mammalian cells often synthesize glycoproteins carrying oligosaccharides with structures that are resistant to all of the above-mentioned endo-β-N-acetylglucosaminidases, e.g., tri- or tetraantennary complex oligosaccharides. If such a glycoprotein is being produced in a cultured cell system, it is possible to block the later stages of oligosaccharide processing by adding oligosaccharide processing inhibitors to the culture medium. Two preferred processing inhibitors are deoxymannojirimycin and swainsonine. Cells treated with one of these inhibitors will preferentially synthesize N-linked oligosaccharides with Endo H-sensitive structures. Deoxymannojirimycin inhibits Mannosidase I, thereby blocking further modification of high-mannose N-linked oligosaccharides. Swainsonine is a Mannosidase II inhibitor, blocking the removal of the two α-linked mannose residues on the α1→6-linked mannose residue of the Man$_3$GlcNAc$_2$ core (i.e., conversion of structure M-d to structure M-e in FIG. 2). As a result, glycosylated Asn residues which would normally carry Endo H-resistant complex type glycans will carry Endo H-sensitive "hybrid" oligosaccharides instead. Swainsonine and deoxymannojirimycin are both commercially available, for example from Genzyme Corp., Boston Mass., or Boehringer Mannheim, Indianapolis Ind. In most cases, the altered glycoproteins produced in the presence of deoxymannojirimycin or swainsonine will still be secreted in biologically active form. The use and properties of swainsonine and deoxymannojirimycin, as well as those of other oligosaccharide processing inhibitors, have been reviewed by Schwartz and Datema, *Adv. Carbohyd. Chem. Biochem.* 40, 287-379 (1982) and by Fuhrmann et al., *Biochim. Biophys. Acta* 825, 95-110 (1985).

Oligosaccharide processing inhibitors that block Glucosidases I or II, such as deoxynojirimycin or castanospermine, which are both available from Genzyme Corp., Boston Mass., will also generate Endo H-sensitive structures, but these inhibitors are less preferred because they sometimes block secretion. Many other oligosaccharide processing inhibitors, described in the two reviews cited in the previous paragraph, will also serve the same purpose.

d. Cleavage by endo-β-N-acetylglucosaminidases after production of a glycoprotein in a mutant cell line. Another approach for manipulating the structures of the N-linked oligosaccharides of a glycoprotein is to express it in cells with one or more mutations in the oligosaccharide processing pathways. Such mutations are readily selected for in mammalian cells. A number of techniques have been used to generate processing mutants, but selection for resistance or hypersensitivity to one or more of a variety of lectins, as an indicator of the presence of a processing mutation, has been one useful approach. DNA coding for a glycoprotein(s) can be introduced into such a mutant cell line using conventional methods (e.g., transformation with an expression vector containing the DNA). Alternatively, a mutant subline with defective processing can be selected from a line already capable of producing a desired glycoprotein.

Depending on the desired phenotype, any of a wide variety of mutant cell lines can be used. For example, there are perfectly viable, fast-growing GlcNAc$_2$ transferase I mutants of both CHO cells (an established Chinese hamster ovary cell line long used for mutational studies and mammalian protein expression) and BHK-21 cells (an established line of baby hamster kidney origin). Both CHO and BHK-21 cells are available from the American Type Culture Collection, Rockville Md. Because of the missing enzyme activity, the mutant cells are unable to synthesize any complex or hybrid N-linked oligosaccharides; glycosylated Asn residues which would normally carry such glycans carry Man$_5$GlcNAc$_2$ instead. Thus, glycosylated Asn residues carry only . Man$_{5-9}$ GlcNAc$_2$, all structures which are sensitive to Endo H. Many other mutant cell lines have also been characterized, examples of which include lines with various defects in fucosylation, a defect in galactosylation resulting in failure to extend the outer branches past the GlcNAc$_2$ residues, an inability to add extra branches to produce tri- and tetraantennary complex oligosaccharides, and various defects in Ser/Thr-linked glycan synthesis. The subject of processing-defective animal cell mutants has been reviewed by Stanley, in *The Biochemistry of Glycoproteins and Proteoglycans*, edited by Lennarz, Plenum Press, New York, 1980.

A series of yeast mutants with various defects in mafinan synthesis has also been produced, as described by Ballou, in *The Molecular Biology of the Yeast Saccharomyces*, edited by Strathern et al., Cold Spring Harbor Laboratory, 1982. Thus, it is possible to produce a glycoprotein in a mutant *S. cerevisiae* strain which cannot elongate high-mannose oligosaccharides into large mannans.

e. Sequential exoglycosidase digestion with or without subsequent cleavage by Endo L or Endo D. An alternative, but less preferred method for generating GlcNAc→Asn(protein) in cases where the glycoprotein contains high-mannose or mannan-type oligosaccharides is to remove monosaccharide units by exoglycosidase digestion with or without subsequent use of Endo L. The first step is digestion with an α-mannosidase to remove all α-linked mannose residues. In the case of mannans from some yeast strains, it may be desirable to include other exoglycosidases or phosphatases if other sugars or phosphate residues are present in the outer portion of the mannan structure. In the second digestion step, the last mannose residue is removed with a β-mannosidase. The product, GlcNAc$_2$→Asn(-protein), is then subjected to the third digestion step, which is carried out with β-hexosaminidase. This enzyme removes the terminal GlcNAc residue to generate GlcNAc→Asn(protein); since the last GlcNAc is linked to the protein by an amide rather than a glycosidic bond, the hexosaminidase cannot remove the innermost GlcNAc residue from the asparagine.

Alternatively, α-mannosidase treatment of high-mannose or mannan-type oligosaccharides can be followed by incubation with Endo L, which can be purified from *Streptomyces plicatus*. This enzyme can cleave between the GlcNAc residues of Manβ1→4GlcNAcβ1→4GlcNAc.

In the case of a glycoprotein containing complex or hybrid-type oligosaccharides, sequential (or, when the requirements of the enzymes make it possible, simultaneous) incubation with the appropriate exoglycosidases,, such as sialidase, $\beta$- and/or $\alpha$-galactosidase, $\beta$-hexosaminidase, and a-fucosidase, will trim the oligosaccharides back to $Man_3GlcNAc_2$. This oligosaccharide can be cleaved by Endo D or Endo F. Alternatively, it can be treated with $\alpha$-mannosidase to generate protein-linked $Man\beta1\rightarrow4GlcNAc\beta1\rightarrow4GlcNAc$. This can be cleaved either with Endo L or with digestions with $\alpha$-mannosidase, $\beta$-mannosidase, and $\beta$-hexosaminidase.

Sialidase can be purified from a variety of sources, including *E. coli, Clostridium perfringens, Vibrio choleras,* and *Arthrobacter urefaciens,* and is commercially available from a number of sources such as Calbiochem-Behring, San Diego Calif. or Sigma Chemical Corp., St. Louis Mo. P-Galactosidase can be purified from *Aspergillus niger, C. perfringens,* jack bean, or other suitable sources and is commercially available from Sigma Chemical Corp., St. Louis Mo. $\alpha$-Galactosidase from *E. coli* or green coffee beans is available from Boehringer Mannheim, Indianapolis Ind. F-Hexosaminidase can be purified from jack bean, bovine liver or testis, or other suitable sources and is also commercially available from Sigma Chemical Corp., St. Louis Mo. $\beta$-Mannosidase has been purified from the snail *Achatina fulica,* as described by Sugahara and Yamashima in *Meth. Enzymol.* 28, 769-772 (1972), and from hen oviduct, as described by Sukeno et al. in *Meth. Enzymol.* 28, 777-782 (1972). a-liannosidase from jack bean is preferred and is commercially available from Sigma Chem. Corp., St. Louis Mo. Endo H, Endo D, and Endo F are commercially available from Genzyme Corp., Boston Mass.; from New England Nuclear, Boston Mass.; from Miles Scientific, Naperville Ill.; or from Boehringer Mannheim, Indianapolis Ind. Conditions for the use of these and the other endo-$\beta$-N-acetylglucosaminidases Endo $C_{II}$ and Endo L are described in the publications cited in Table I.

f. Chemical removal of all sugars except N-linked GlcNAc. It is also possible to generate protein-linked GlcNAc chemically. For example, as described by Kalyan and Bahl in *J. Biol. Chem.* 258, 67-74 (1983), hydrolysis with trifluoromethane sulfonic acid (TFMS) has been used to remove all sugars except the N-linked $GlcNAc_2$ residues while leaving the protein backbone intact. Similar results have been obtained using hydrofluoric acid, as described by Mort and Lamport in *Anal. Biochem.* 82, 289-309 (1977).

Step 2. Attachment of galactose to GlcNAc→Asn(-protein).

In Step 2, the terminal $GlcNAc_2$ residue generated in Step 1 serves as a site for the attachment of galactose. Either of two galactosyltransferases may be used: UDP-Gal:GlcNAc-R $\beta1\rightarrow4$ galactosyltransferase or UDP-Gal:GlcNAc-R $\beta1\rightarrow3$ galactosyltransferase. In the first variation of this step, a $\beta1\rightarrow4$-linked galactose residue is added to GlcNAc→Asn(protein). UDP-Gal:GlcNAc-R $\beta1\rightarrow4$ galactosyltransferase can be obtained from a variety of sources, the most common and cost-effective one being bovine milk. Enzyme from this source is commercially available from Sigma Chem. Corp., St. Louis Mo. The reaction conditions for using the bovine milk galactosyltransferase to transfer galactose from UDP-Gal to GlcNAc→Asn(protein) are similar to those described by Trayer and Hill in *J. Biol. Chem.* 246, 6666-75 (1971) for natural substrates. The preferred reaction pH is 6.0 to 6.5. Most buffers can be used with the exception of phosphate, which inhibits enyzme activity, and a broad range of salt concentrations can be used. It is preferable to have 5-20 mM $Mn^{+2}$ or $Mg^{+2}$ present. Peptidase inhibitors such as phenylmethanesulfonyl fluoride, TPCK, aprotinin, leupeptin, and pepstatin and exoglycosidase inhibitors such as galactono-1,4-lactone can be added without interfering with the activity of the galactosyltransferase.

Since the removal of the carbohydrate from the protein can cause solubility problems, it is sometimes necessary to use relatively high concentrations of a non-ionic detergent such as 2-3% Triton X-100, other suitable solubilizers such as DMSO, or denaturing agents such as 2-3M urea to keep the protein in solution. We have found that this does not interfere with the galactosylation step, the bovine milk $\beta1\rightarrow4$ galactosyltransferase apparently remaining sufficiently active under these conditions.

In the second variation of this step, a $\beta1\rightarrow3$-linked galactose residue is transferred to GlcNAc→Asn(-protein). UDP-Gal:GlcNAc-R $\beta1\rightarrow3$ galactosyltransferase has been purified from pig trachea. Conditions for the use of this enzyme to transfer galactose from UDP-Gal to GlcNAc-R have been described by Sheares and Carlson in *J. Biol. Chem.* 258, 9893-98 (1983).

Step 3. Attachment of sialic acid to $Gal\beta1\rightarrow4(3)GlcRAc\rightarrow Asn$-(protein)

The term "sialic acid" (SA) includes any naturally occurring or chemically synthesized sialic acid or sialic acid derivative. The preferred naturally occurring sialic acid is N-acetylneuraminic acid (NeuAc). As discussed by Schauer in *Adv. Carb. Chem. Biochem.* 40, 131-234 (1982), other sialic acids can also be transferred from CMP-SA to galactose, for example, N-glycolyl neuraminic acid, 9O-acetyl neuraminic acid, and 4-O-acetyl-N-acetyl neuraminic acid. Many other sialic acids such as those described in *Sialic Acids: Chemistry, Metabolism and Function,* edited by R. Schauer (Springer-Verlag, New York, (1982), are potential substrates. There are two variations of the method for attaching sialic acid to the substrate generated in Steps 1 and 2, $Gal\beta1\rightarrow4(3)GlcNAc\rightarrow Asn(protein)$.

In the first of the two variations, the sialic acid is attached to $Gal\beta1\rightarrow4GlcNAc\rightarrow Asn(protein)$ in an $\alpha2\rightarrow6$ linkage. The CMP-SA:-$Gal\beta$ 1→4GlcNAc-R $\alpha2\rightarrow6$ sialyltransferase used in this step can be obtained from a variety of sources, the more usual ones being bovine colostrum and rat liver. The rat liver enzyme has recently become commercially available from Genzyme Corp., Boston Mass.

The reaction conditions for using the bovine colostrum and rat liver $\alpha2\rightarrow6$ sialyltransferases to transfer sialic acid from CMP-SA to $Gal\beta1\rightarrow4GlcNAc\rightarrow Asn(-protein)$ are similar to those described by Paulson et al. in *J. Biol. Chem.* 252, 2356-62 (1977) for natural substrates, except that it may be desirable to add additional enzyme to accelerate the rate of the reaction. The preferred pH is 6.5-7.0. Although most buffers, with the exception of phosphate, can be employed, preferred buffers are Tris-maleate or cacodylate. The enzyme is functional in the presence of mild detergents such as NP-40 and Triton X-100; peptidase inhibitors such as phenylmethanesulfonyl fluoride, TPCK, aprotinin, leupeptin and pepstatin; and exoglycosidase inhibitors such as galactono-1,4-lactone.

In the second variation of this step, the sialic acid is attached to the Galβ1→4(3)GlcNAc→Asn(protein) by an α2→3 linkage. Two sialyltransferases producing this linkage have been described. The first, CMP-SA:-Galβ1→4GlcNAc α2→3 sialyltransferase, has been identified in human placenta by van den Eijnden and Schiphorst as described in *J. Biol. Chem.* 256, 3159-3162 (1981). This enzyme, although not yet purified, can be purified using conventional methods. The second enzyme, CMP-SA:Galβ1→3(4)GlcNAc α2→3 sialyltransferase, has been purified from rat liver by Weinstein et al. as described in *J. Biol. Chem.* 257, 13835-44 (1982). The rat liver enzyme has a somewhat relaxed specificity and is able to transfer sialic acid from CMP-sialic acid to the C-3 position of galactose in both Galβ1→4-GlcNAc and Galβ1→3GlcNAc sequences. Conditions for the use of the α2→3 sialyltransferases are described in the two publications just cited.

B. Method for preparing glycoproteins containing SA→Gal→GlcNAc→GlcNAc→Asn(protein)

The method used to generate SA→Gal→GlcNAc→GlcNAc→ Asn(protein) is similar to the method described above for generating modified glycoproteins containing the trisaccharide sequence SA→Gal→GlcNAc→Asn(protein). In the preferred embodiment, both core GlcNAc$_2$ residues of the original N-linked oligosaccharide are left attached to the protein and a tetrasaccharide sequence, SA→Gal→GlcNAc→GlcNAc→ is constructed enzymatically.

Step 1. Generation of GlcNAcβ1→4GlcNAc→Asn(protein)

The intact N-linked oligosaccharide chain is treated with exoglycosidases selected to remove all carbohydrate exterior to the two innermost GlcNAc residues. In the case of high-mannose or mannan-type oligosaccharides, α- and β-mannosidase are used. In the case of complex or hybrid-type oligosaccharides, additional exoglycosidases are required, the specific enzymes used depending on the structures of the carbohydrate chains being modified. In most cases, treatments with sialidase, β- and/or α-galactosidase, β-hexosaminidase, and if necessary, α-fucosidase, are carried out in addition to treatment with α- and β-mannosidase. The β-hexosaminidase treatment is intended to remove GlcNAc residues only from the outer branches of the oligosaccharides, not from the core, and care should be taken that no β-hexosaminidase is present during or after β-mannosidase treatment. The reaction conditions and sources of the exoglycosidases are identical to those described above for Step 1 in the generation of SA→Gal→GlcNAc→Asn(protein).

The methods used to attach galactose to GlcNAcβ1→4GlcNAc→Asn-(protein) and sialic acid to Galβ1→4(3)GlcNAcβ1→4GlcNAc→Asn-(protein) are the same as those described earlier for the preparation of modified glycoproteins containing N-linked SAα2→3(6)Galβ1→4(3)-GlcNAc→Asn(protein).

C. Method for attaching oligosaccharides to non-glycosylated amino acid residues of proteins The principal method for attaching oligosaccharides such as SA→Gal→GlcNAc→ to non-glycosylated amino acid residues is to react an activated glycoside derivative of what is to be the innermost sugar residue, in this case GlcNAc, with the protein and then to use glycosyltransferases to extend the oligosaccharide chain. Chemical and/or enzymatic coupling of glycosides to proteins can be accomplished using a variety of activated groups, for example, as described by Aplin and Wriston in *CRC Crit. Rev. Biochem.*, pp. 259-306 (1981). The advantages of the chemical coupling techniques are that they are relatively simple and do not need the complicated enzymatic machinery required for natural N-linked glycosylation. Depending on the coupling mode used, the sugar(s) can be attached to arginine, histidine, or the amino-terminal amino acid of the polypeptide; (b) free carboxyl groups, such as those of glutamic acid or aspartic acid or the carboxyterminal amino acid of the polypeptide; (c) free sulfhydryl groups, such as those of cysteine; (d) free hydroxyl groups, such as those of serine, threonine, or hydroxyproline; (e) aromatic residues such as those of phenylalanine, tyrosine, or tryptophan; or (f) the amide group of glutamine.

As shown below, the aglycone, R, is the chemical moiety that combines with the sugar to form a glycoside and which is reacted with the amino acid to bind the sugar to the protein.

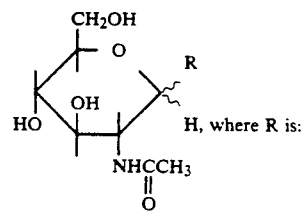

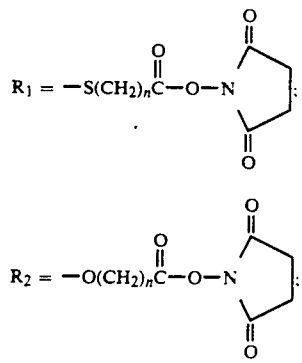

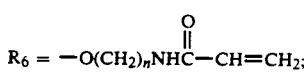

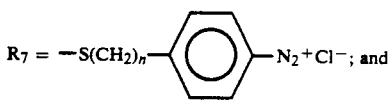

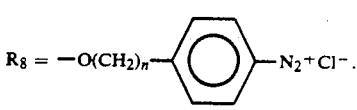

GlcNAc residues can be attached to the ε-amino groups of lysine residues of a nonglycosylated protein by treating the protein with 2-imino-2-methyoxyethyl-1-thio-β-N-acetylgl-ucosaminide as described by Stowell and Lee in *Meth. Enzymol.* 83, 278-288 (1982).

Other coupling procedures can be used as well, such as treatment of the protein with a glycoside or thioglycoside derivative of GlcNAc in which the aglycone contains an activated carboxylic acid, for example $R_1$ or $R_2$.

GlcNAc residues can be attached to the carboxyl groups of aspartic acid and glutamic acid residues of a nonglycosylated protein by treatment of the protein with a glycoside or thioglycoside derivative of GlcNAc in which the aglycone contains a free amino group, for example $R_3$ or $R_4$, in the presence of a coupling reagent such as a carbodiimide.

Compounds which contain free amino groups, for example GlcNAc derivatives containing the aglycones $R_3$ or $R_4$, can also be used to derivatize the amide groups of glutamine through the action of transglutaminase as described by Yan and Wold in *Biochemistry* 23, 3759-3765 (1984).

Attachment of GlcNAc residues to the thiol groups of the cysteine residues of a nonglycosylated protein can be accomplished by treating the protein with a GlcNAc glycoside or thioglycoside in which the aglycone contains an electrophilic site such as an acrylate unit, for example the aglycones $R_5$ or $R_6$.

The glycosylation of aromatic amino acid residues of a protein with a monosaccharide such as GlcNAc can be accomplished by treatment with a alycoside or thioglycoside in which the aglycone contains a diazo group, for example aglycones $R_7$ or $R_8$.

A large number of other coupling methods and aglycone structures can be employed to derivatize a protein with a GlcNAc derivative.

After chemical derivatization of the protein with GlcNAc residues, the trisaccharide sequence SAα2→3(6)Galβ1→4(3)GlcNAc→ is constructed by sequential enzymatic attachment of galactose and sialic acid residues, as described for Asn-linked GlcNAc residues.

In other variations, the protein is derivatized with:
Galβ1→4(3)GlcNAc-X,
Galβ1→4(3)GlcNAcβ1→4GlcNAc-X,
SAα2→3(6)Galβ1→4(3)GlcNAc-X, or
SAα2→3(6)Galβ1→4(3)GlcNAcβ1→4GlcNAc-X,
where X is an aglycone containing a free amino group, an activated ester of a carboxylic acid, a diazo group, or other groups described above.

The same procedures may be used to chemically attach galactose, rather than GlcNAc, directly to an amino acid. The galactose may then be enzymatically extended or capped with sialic acid, as previously described.

D. Generation of additional protein-linked oligosaccharides by elongation of GlcNAc-protein or GlcNAc→GlcNAc-protein.

Procedures similar to those used to extend GlcNAc-protein or GlcNAc→GlcNAc-protein to a protein-linked oligosaccharide resembling the outer branch of a complex oligosaccharide can be employed to construct other carbohydrate structures found on GlcNAc residues attached to the terminal mannose units of the core pentasaccharide.

Example 1. Generation of proteins containing repeating units of (GlcNAcβ1→3Galβ1→4). After preparation of either GlcNAc-protein or GlcNAcβ1→4GlcNAc-protein using the methods described above, a long carbohydrate chain may be generated by several rounds of alternating UDP-Gal:GlcNAc-R β1→4 galactosyltransferase and UDP-GlcNAc:Galβ1→4GlcNAc-R β1→3 N-acetylglucosaminyltransferase incubations. This will generate a polylactosaminyl-type structure of the type (GlcNAcβ1→3Galβ1→4)$_n$ attached to the GlcNAc-protein or GlcNAcβ1→4GlcNAc-protein starting material. Kaur, Turco and Laine reported in *Biochemistry International* 4, 345-351 (1982) that bovine milk UDP-Gal:GlcNAc β1→4 galactosyltransferase can transfer the β1→4-linked galactosyl residues to polylactosaminyl oligosaccharides, and a β1→3 N-acetylglucosaminyltransferase has been identified in Novikoff ascites tumor cells by van den Eijnden et al., *J. Biol. Chem.* 258, 3435-37 (1983). The number of repeating GlcNAc→Gal units in the structure can be varied depending on the desired length; 1-10 such units should suffice for most applications. The essential element is that, after attachment of the disaccharide units, an exposed galactose residue is present so that the carbohydrate chain can be capped with α2→3- or α2→6-linked sialic acid as described above. Thus, the final structure would be SAα2→6(3)Galβ1→4[GlcNAcβ1→3Galβ1→4]$_n$GlcNAc-protein, or SAα2→6(3)Galβ1→4[GlcNAcβ1→3Galβ1→4]$_n$GlcNAcβ1→4GlcNAc-protein, protein, where n is 1-10.

The advantages of introducing such a polylactosaminyl structure would be to increase solubility or to better mask the protein backbone to protect it from recognition by the immune system or from degradation by proteases.

Example 2. Generation of glycoproteins containing terminal
Galβ1→4(3)[Fucα1→3(4)GlcNAc or
SAα2→3Galβ1→3(Fucα1→4)GlcNAc
structures. After preparation of
Galβ1→4(3)GlcNAc-protein,
Galβ1→3(4)[GlcNAcβ1→3Galβ1→4]$_n$GlcNAc-protein,
Galβ1→4(3)GlcNAcβ1→4GlcNAc-protein,
Galβ1→3(4)[GlcNAcβ1→3Galβ1→4]$_n$GlcNAcβ1→4GlcNAc-protein,
SAα2→3Galβ1→3GlcNAc-protein,
SAα2→3Galβ1→3[GlcNAcβ1→3Galβ1→4]$_n$GlcNAc-protein,
SAα2→3Galβ1→3GlcNAcβ1→4GlcNAc-protein
or
SAα2→3Galβ1→3[GlcNAcβ1→3Galβ1→4]$_n$GlcNAcβ1→4GlcNAc-protein
where n is between 1 and 10, using the methods described above, a fucose can be attached to any of the acceptor GlcNAc residues by treatment with GDP-Fuc and a GDP-Fuc:-GlcNAc α1→3(4) fucosyltransferase. The purification of this fucosyltransferase, its substrate specificity and preferred reaction conditions have been reported by Prieels et al in *J. Biol. Chem.* 256, 104456-63 (1981). The activity of this enzyme with sialylated substrates has been described by Johnson and Watkins in Proc. VIIIth Int. Symp. Glycoconjugates (1985), eds. E. A. Davidson, J. C. Williams and N. M. Di Ferrante. If it is desired to attach fucose only in an α1→3 linkage to the appropriate acceptor GlcNAc residues, the GDP-Fuc:GlcNAc α1→3 fucosyltransferase can be used. This enzyme has been described by Johnson and Watkins in *Proc. VIIIth Int. Symp. Glycoconjugates* (1985), eds. E. A. Davidson, J. C. Williams and N. M. Di Ferrante.

E. Targeting of glycosylated proteins to specific cells

Cells with sugar-specific cell surface receptors are able to recognize and internalize glycoproteins bearing appropriate carbohydrate structures. The best characterized sugar-specific cell surface receptors are the Gal receptor of hepatocytes, the Man/GlcNAc receptor of reticulo-endothelial cells and the fucose receptor found on hepatocytes, lymphocytes and teratocarcinoma cells. The subject of sugar-specific cell surface receptors has been reviewed by Neufeld and Ashwell in *The Biochemistry of Glycoproteins and Proteoglycans*, edited by Lennarz, Plenum Press, New York (1980), pp. 241-266.

Proteins can be targeted to cells with sugar-specific cell surface receptors by generating glycoproteins that contain the appropriate sugar at nonreducing terminal positions. Several procedures are used to expose the desired terminal sugars. One procedure, in general, involves the treatment of a native glycoprotein with exoglycosidases, as described by Ashwell and Morell in *Adv. Enzymol.* 41, 99-128 (1974). Another procedure is the attachment of monosaccharides to the protein, as described by Stahl et al. in *Proc. Natl. Acad. Sci. USA* 75, 1399-1403 (1978). A third approach is the attachment of derivatives of oligosaccharides isolated from natural sources such as ovalbumin, as reported by Yan and Wold in *Biochemistry* 23, 3759-3765 (1984). The glycosylated proteins that are the subject of the present invention can be targeted to specific cells, depending on the specific sugars attached.

Gal→GlcNAc-protein,
Gal→GlcNAc→GlcNAc-protein,
(Gal→GlcNAc)$_n$Gal→GlcNAc-protein and
(Gal→GlcNAc)$_n$Gal→GlcNAc→GlcNAc-protein,
where n is 1-10, are directed to hepatocytes.
GlcNAc-protein,
GlcNAc→GlcNAc-protein,
(GlcNAc→Gal)$_n$GlcNAc-protein and
(GlcNAc→Gal)$_n$GlcNAc→GlcNAc-protein,
where n is 1-10, are targeted to macrophages. Finally,
Gal→(Fuc→)GlcNAc-protein,
Gal→(Fuc→)GlcNAc→GlcNAc-protein,
Gal→(Fuc→)GlcNAc→[Gal→(Fuc→)$_m$GlcNAc]$_n$-protein, and
Gal→(Fuc→)GlcNAc→[Gal→(Fuc→)$_m$GlcNAc]$_n$GlcNAc-protein,
where n is 1-10 and m is 0 or 1, are targeted to hepatocytes, lymphocytes and teratocarcinoma cells. One application of targeting is for enzyme replacement therapy. For example, glucocerebrosidase can be targeted to macrophages for the treatment of Gaucher's disease. A second application is to target drugs or toxins to teratocarcinoma cells.

The following non-limiting example demonstrates the method of the present invention on a yeast glycoprotein possessing multiple high-mannose and mannan oligosaccharides.

Step 1. Endo H treatment of yeast external invertase.

Yeast external invertase is a glycoprotein containing approximately two high mannose and seven mannan oligosaccharides. External invertase of a commercial preparation from *Saccharomyces cerevisiae*, obtained from Sigma Chem. Corp, St. Louis Mo., was purified as described by Tremble and Maley in *J. Biol. Chem.* 252, 4409-12 (1977), and treated with Endo H essentially as described by Tremble et al. in *J. Biol. Chem.* 258, 2562-67 (1983). The purified invertase was denatured by placing a 1% SDS solution of the glycoprotein in a boiling water bath for 5 minutes. The denatured invertase (250 μg) was then incubated with Endo H (0.3 μg, from Miles Scientific, Naperville Ill.) for 20 hours at 37° C. in 175 μl of 0.1M sodium citrate buffer, pH 5.5. After Endo H treatment, the reaction mixture was desalted on a Bio-Gel P-4 column (1×10 cm) equilibrated and eluted with 50 mM ammonium acetate, pH 6.5. The method of desalting is not critical. Dialysis or protein precipitation can also be used. The material eluting in the void volume of the column was pooled and lyophilized.

Figure 3:
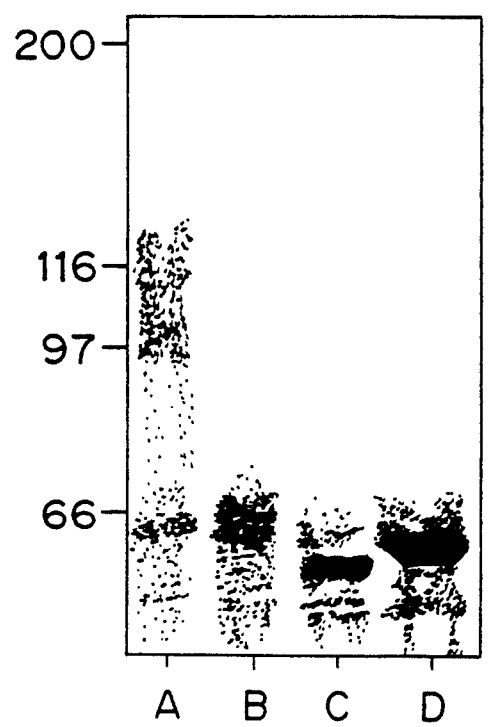
FIG. 3 is a Coomassie blue-stained gel prepared by sodium dodecylsulfate-polyacrylamide gel electrophoresis (SDS-PAGE) of yeast external invertase before and after treatment with glycosidases. The acrylamide concentration was 6%. (A) untreated invertase; (B) invertase after treatment with Endo H under non-denaturing conditions; (C) invertase after Endo H treatment under denaturing conditions (0.7% SDS); and (D) an aliquot of a sample first treated with Endo H under non-denaturing conditions and subsequently treated with jack bean α-mannosidase.

Analysis of the Endo H-treated preparation of SDS-denatured invertase by SDS-PAGE, shown in FIG. 3c, indicated that the glycoprotein had been converted to a form consistent with an invertase possessing only a single GlcNAc residue at each glycosylation site.

In a parallel experiment, native invertase was treated with Endo H in the same manner as the SDS-denatured invertase. Analysis of the desalted reaction product by SDS-PAGE, shown in FIG. 3b, indicated that 2-3 oligosaccharide chains of native invertase were resistant to cleavage by Endo H. To remove exposed mannose residues on the resistant chains, 250 μg Endo H-treated invertase was desalted, lyophilized, and incubated in 100 μl of 50 mM sodium acetate, pH 5.0, containing 50 mM NaCl, 4 mM ZnCl and 20 mU of jack bean α-mannosidase (a gift from Dr. R. Trimble at State University of New York, Albany N.Y.) for 17 hours at 37° C. Analysis of the reaction mixture by SDS-PAGE, shown in FIG. 3d, demonstrated through a shift to lower molecular weight that the α-mannosidase treatment removed additional mannose residues.

Step 2. Galactosylation of the Endo H-treated samples of native and denatured yeast Aternal invertase.

Figure 4:
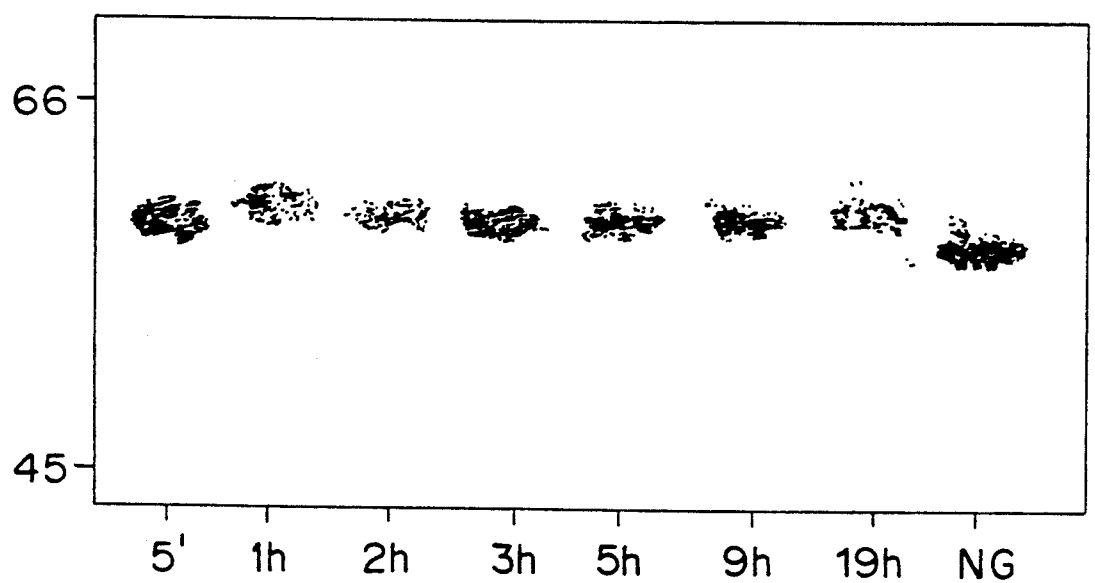
FIG. 4 is a fluorogram of a 6% SOS-PAGE gel of samples of yeast external invertase removed at intervals (5 min, 1 hr, 2 hr, 3 hr, 5 hr, 9 hr and 19 hr) during galactosylation of Endo H-treated, SDS-denatured invertase (FIG. 3B) with UDP-[$^3$H]Gal and bovine milk β1→4 galactosyltransferase.
Figure 5:
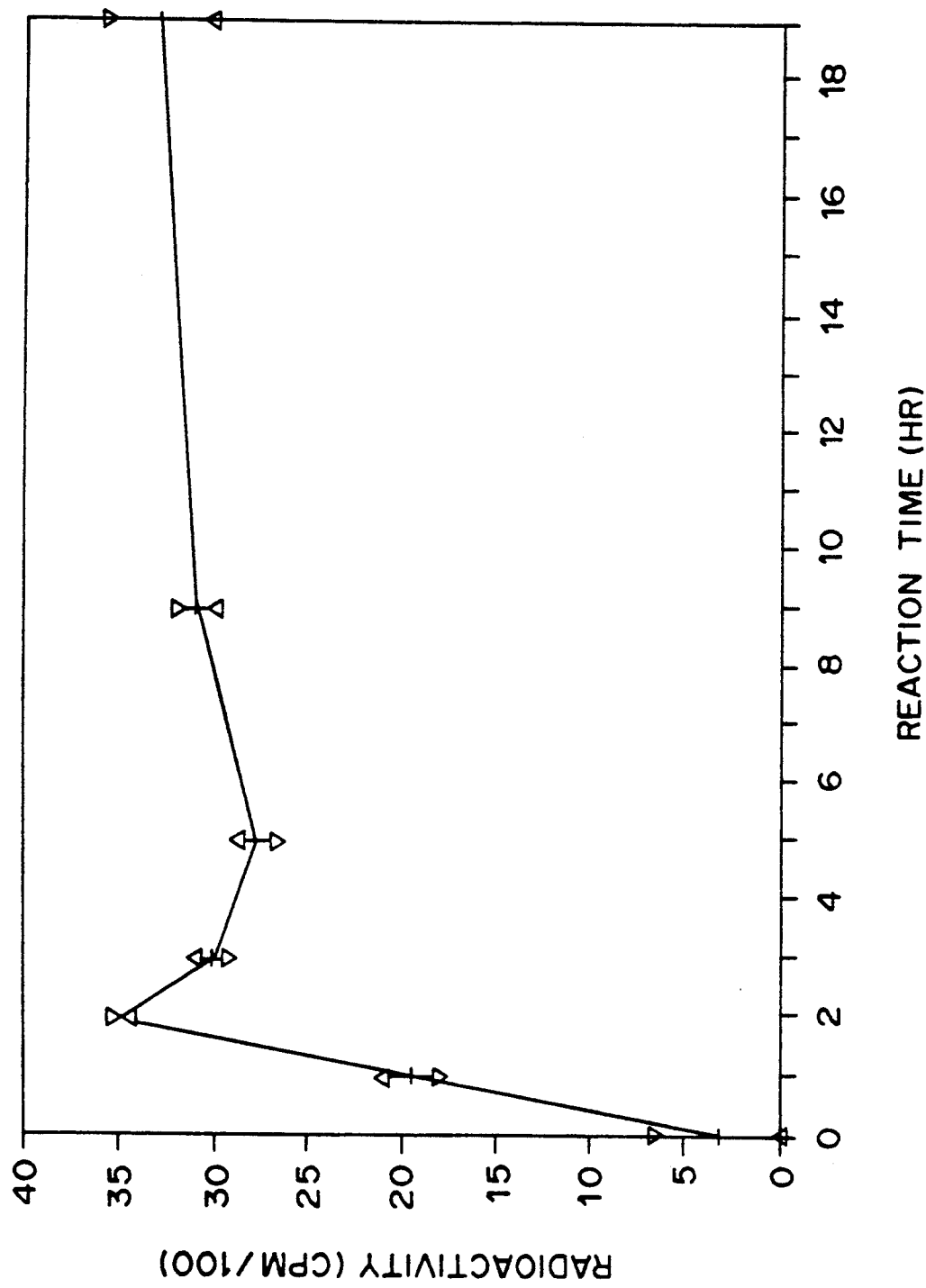
FIG. 5 shows the rate of incorporation of acid-precipitable radioactivity into Endo H-treated, SDS-denatured yeast external invertase during treatment with UDP-[$^3$H)Gal and bovine milk β1→4 galactosyltransferase.

An Endo H-treated sample of denatured yeast external invertase [85 μg, containing approximately 15 nmol of GlcNAc→Asn(protein) sites] was incubated at 37° C. in 180 μl of 50 mM 2-(N-morpholino)ethanesulfonic acid (MES), pH 6.3, containing 0.8% Triton X-100, 25 mM MnCl$_2$, 1.25 mM UDP-[$^3$H]Gal (specific activity, 8 Ci/mol) and bovine milk UDP-Gal:GlcNAc β1→4 galactosyltransferase (100 mU, Sigma Chem. Corp., St. Louis Mo.). Aliquots were removed at selected times and analyzed by SDS-PAGE, as shown in FIG. 4. A gradual increase in apparent molecular weight was apparent up to a reaction time of one hour. This result was confirmed by measuring the incorporation of tritium into material precipitable by 0.5M HCl/1% phosphotungstic acid, which gave the result shown in FIG. 5.

Nonradiolabeled galactosylated samples of native and denatured yeast external invertase were prepared as substrates for the sialylation reaction. Endo H-treated denatured invertase and Endo H plus α-mannosidase-treated native invertase were galactosylated with nonradioactive UDP-Gal using the procedures described above.

Step 3. Sialylation of the galactosylated samples of native and denatured yeast external invertase.

Figure 6:
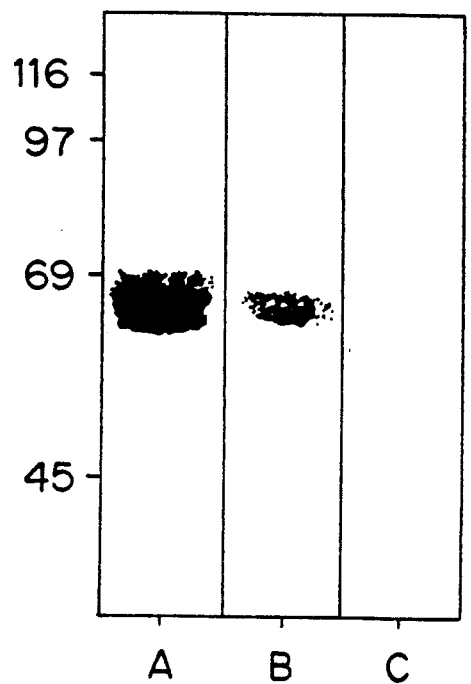
FIG. 6 is an autoradiogram of a 6% SDS-PAGE gel of various yeast external invertase derivatives that have been sialylated using CMP-[$^{14}$C]NeuAc and bovine colostrum a2→6 sialyltransferase. (A) Sialylation product derived from galactosylated, Endo H-treated, SDS-denatured invertase; (B) sialylation product derived from a galactosylated sample of Endo H- and Jack bean a-mannosidase-treated, non-denatured invertase; (C) sialylation product derived from untreated invertase.

The native and denatured samples of nonradioactive galactosylated yeast external invertase (50 μg of protein) were incubated at 37° C. for 17 hours in 70 μl of 0.1M Tris-maleate, pH 6.7, containing 0.7% Triton X-100, 2 mM CMP-[$^{14}$C]NeuAc (specific activity, 1.1 Ci/mmol) and bovine colostrum CMP-SA:-Galβ1→4GlcNAc-R α2→6 sialyltransferase [1.1 mU, purified according to Paulson et al. in *J. Biol. Chem.* 252, 2356-2362 (1977) The reaction mixtures were analyzed by SDS-PAGE and autoradiography, as shown in FIG. 6. The radioactivity associated with the invertase band demonstrates that sialic acid has been attached to the galactose residues of the invertase by the α2→6 sialyltransferase.

The following non-limiting example demonstrates the method of the present invention using chemical and enzymatic techniques on a protein that is not glycosylated in its native form.

Step 1. Chemical attachment of a thioglycoside derivative of GlcNAc to bovine serum albumin (BSA).

BSA was derivatized by treatment with 2-imino-2-methoxyethyl-1-thio-N-acetylglucosaminide by Dr. R. Schnaar at Johns Hopkins University according to the procedure described by Lee et al. in *Biochemistry* 15, 3956-63 (1976). The glycosylated BSA contained, on the average, 48 lysine-linked GlcNAc residues per molecule.

Step 2. Galactosylation of GlcNAc$_{48}$-BSA.

GlcNAc$_{48}$-BSA (0.9 mg) was incubated at 37° C. for 17 hours in 600 μl of 0.12M MES, pH 6.3, containing 0.6% Triton X-100, 20 mM MnCl$_2$, 5 mM UDP-[$^3$H]Gal (specific activity, 1 Ci/mol), 1 mM galactono-1,4-lactone, 1 mM phenylmethanesulfonyl fluoride, TPCK (21 μg), aprotinin (12 μTIU), leupeptin (0.6 μg), pepstatin (0.6 μg) and bovine milk UDP-Gal:GlcNAc-R β1→4 galactosyltransferase. The glycosylated BSA was partially purified from other reaction components by Bio-Gel P-4 gel filtration. After measurement of the amount of radioactivity incorporated into the BSA, it was calculated that 46% of the available GlcNAc residues were galactosylated. A second incubation of the galactosylated BSA under identical conditions increased the extent of reaction from 46 to 51%. The galactosylated BSA was purified with an anti-BSA antibody column obtained from Cooper Biomedical, Malvern Pa.

Step 3. Sialylation of galactosylated BSA.

The galactosylated BSA (240 μg) was incubated for 16 hours at 37° C. in 120 μl of 0.1M Tris-maleate, pH 6.7, containing 3 mM CMP-[$^{14}$C]NeuAc (specific activity 0.55 Ci/mol) and bovine colostrum CMP-SA:-Galβ1→4GlcNAc-R α2→6 sialyltransferase (2.1 mU). The glycosylated BSA was partially purified from other reaction components by gel filtration. After measurement of the ratio of $^{14}$C to $^3$H radioactivity incorporated into the samples, it was calculated that 42% of the Gal→GlcNAc→protein residues were sialylated. A second incubation of the sialylated BSA with 25 mU of sialyltransferase increased the extent of sialylation to 51%. The glycoprotein was isolated by immunoaffinity chromatography on an anti-BSA antibody column.

Figure 7:
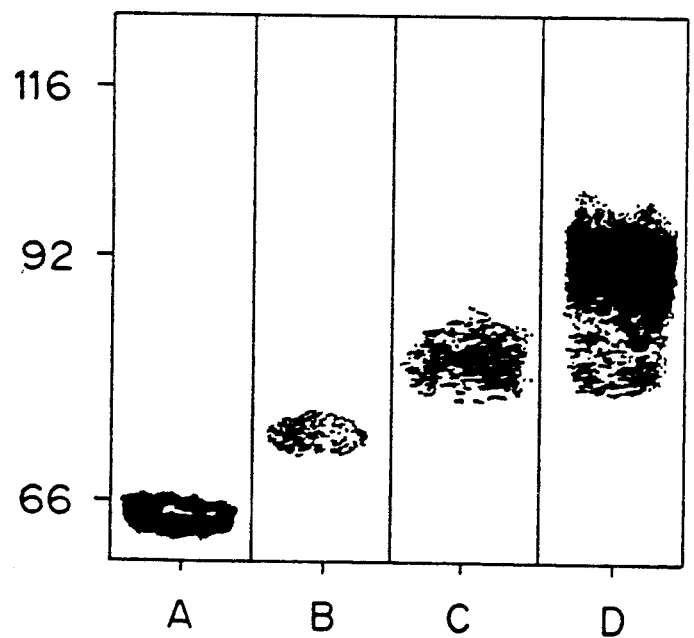
FIG. 7 is a Coomassie blue-stained 6% SDS-PAGE gel of (A) untreated bovine serum albumin (BSA); (B) BSA converted to GlcNAc-BSA containing approximately 48 GlcNAc$_2$ residues per molecule of protein by incubation with 2-imino-2-methoxyethyl-1-thio-N-acetylglucosaminide in 0.25M sodium borate pH 8.5 for 24 hr at room temperature; (C) galactosylated BSA formed by treatment of GlcNAc-BSA with UDP-[$^3$H]Gal and bovine milk β1→4 galactosyltransferase; and (D) sialylated BSA formed by treatment of Gal→GlcNAc-BSA with CMP-[$^{14}$C]NeuAc and bovine colostrum α2→6 sialyltransferase.

Analysis of the three glycosylated forms of BSA by SDS-PAGE demonstrated a significant increase in apparent molecular weight after each step of the procedure, as shown in FIG. 7. This evidence confirms that SA→Gal→GlcNAc→ moieties have been constructed on the protein.

The following nonlimiting example demonstrates the differential uptake of GlcNAc-BSA and Galβ1→4GlcNAc-BSA by GlcNAc/Man-specific receptors of macrophages.

Mouse peritoneal macrophages, which possess cell surface receptors that recognize terminal GlcNAc and Man residues, were obtained from mice 4-5 days after intraperitoneal injection of thioglycollate broth (1.5 ml per mouse). The peritoneal cells were washed with Dulbecco's modified minimal essential medium (DME) containing 10% fetal calf serum (FCS) and plated in 96-well tissue culture trays at a density of 2×10$^5$ cells per well. After 4 hours the wells were washed twice with phosphate-buffered saline (PBS) to remove nonadherent cells. The adherent cells remaining in the wells were used for uptake experiments with GlcNAc-[$^{125}$I]BSA and Galβ1→4GlcNAc-[$^{125}$I]BSA which had been radiolabeled with $^{125}$I by the chloramine T method. The radiolabeled protein preparations were added at a concentration of 0.1-1.2 μg/ml to 100 μl of DME containing 10% FCS and 10 mM HEPES [4-(2-hydroxyethyl)-1-piperazine ethanesulfonic acid], pH 7.4. Parallel experiments were run in the presence of yeast mannan (1 mg/ml) to measure nonspecific uptake of the glycosylated BSA samples. The cells were incubated with the samples for 30 min at 37° C. and then washed five times with PBS to remove residual protein not taken up by the cells. The washed cells were dissolved in 200 μl of 1% SDS and the radioactivity determined. Nonspecific uptake (CPM in the presence of yeast mannan) was subtracted from the total uptake (CPM in the absence of yeast mannan) to determine Man/GlcNAc receptor-specific uptake by the mouse peritoneal macrophages.

Figure 8:
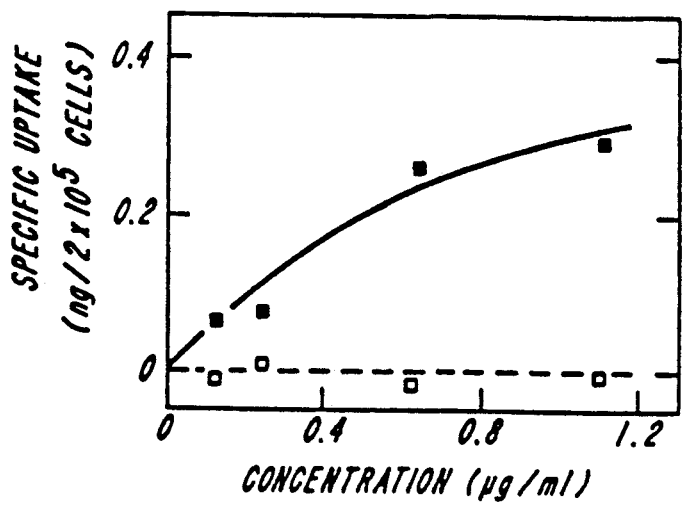
FIG. 8 is a graph of specific uptake (ng/2×10$^5$ cells) of Gal→GlcNAc-[$^{125}$I]BSA (□) and GlcNAc-[$^{125}$I]BSA (■) by the Man/GlcNAc receptor of thioglycollate-elicited mouse peritoneal macrophages as a function of the concentration of glycosylated BSA (μg/ml), where specific uptake is equal to total uptake (uptake in the absence of mannan) minus non-specific uptake (value obtained in the presence of mannan).

The specific uptake of GlcNAc-[$^{125}$I]BSA and Galβ1→4GlcNAc-[$^{125}$I]BSA is presented as a function of BSA concentration in FIG. 8. The results demonstrate that GlcNAc-BSA, but not Galβ1→4GlcNAc-BSA, is recognized and endocytosed by mouse peritoneal macrophages.

The following non-limiting example demonstrates the differential uptake of Galβ1→4GlcNAc-BSA and SAα2→6Galβ1→4GlcNAc-BSA by galactose-specific receptors of hepatoma cell line HepG2.

Samples of GlcNAc-BSA and Gal→GlcNAc-BSA were radiolabeled with $^{125}$I by the chloramine T method. HepG2 cells were cultured in DME containing 10% fetal calf serum. Uptake experiments were performed on cells plated in 35 mm tissue culture dishes at approximately 70% confluency. The cells were washed with protein-free medium and incubated with 1 ml of DME containing 20 mM HEPES, pH 7.3, containing cytochrome c (0.2 mg/ml) and 0.5-7.5 μg of Galβ1→4GlcNAc-[$^{125}$I]BSA or SAα2→6Galβ1→4GlcNAC-[$^{125}$I]BSA. Parallel experiments were performed in the presence of nonradioactive asialo-orosomucoid (0.2 mg/ml) to determine nonspecific uptake. The cells were incubated with the radiolabeled protein solutions for 2.5 hours at 37° C. in a 5% CO$_2$ atmosphere, and then rinsed five times with chilled PBS containing 1.7 mM Ca$^{++}$. The washed cells were solubilized with 1 ml of 1M NaOH/10% SDS. Separate aliquots were used to measure radioactivity and the amount of protein per culture dish. It is assumed that the amount of protein in each dish is proportional to the number of cells. Non-specific uptake (CPM in the presence of asialo-orosomucoid) was subtracted from the total uptake (CPM in the absence of asialoorosomucoid) to determine the galactose receptor-specific uptake by the HepG2 cells.

Figure 9:
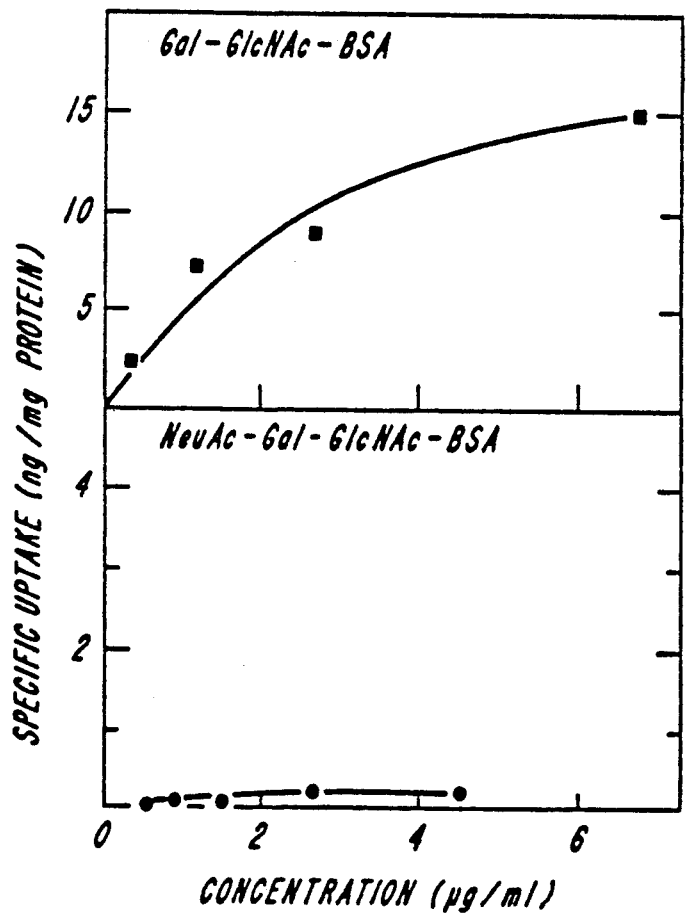
FIG. 9 is a graph of specific uptake (ng/mg cellular protein) of Gal→GlcNAc[$^{125}$I]BSA (■) and NeuAc→Gal→GlcNAc-[$^{125}$I]BSA (•) by the Gal/GalNAc$_2$ receptor of HepG2 cells vs. protein concentration (0.5 to 7.5 μg protein/ml), where specific uptake is equal to total uptake (uptake in the absence of asialo-orosomucoid) minus non-specific uptake (value obtained in the presence of asialo-orosomucoid).

The galactose receptor-specific uptake is shown as a function of glycosylated BSA concentration in FIG. 9. The results demonstrate that Galβ1→4GlcNAc-BSA, but not SAα2→6Galβ1→4GlcNAc-BSA, is recognized and endocytosed by HepG2 cells.

The following non-limiting example demonstrates the method of the present invention on a mammalian glycoprotein having one oligosaccharide chain of the high-mannose type.

Step 1. Deglycosylation of ribonuclease B, a glycoprotein having a single high-mannose oligosaccharide.

Native ribonuclease B (490 μg), obtained from Sigma Chem. Corp., St. Louis Mo., and further purified by concanavalin A affinity chromatography as described by Baynes and Wold in *J. Biol. Chem.* 251, 6016–24 (1976) was incubated with Endo H (50 mU, obtained from Genzyme Corp., Boston Mass.) in 100 μl of 50 mM sodium acetate, pH 5.5, for 24 hours at 37° C. SDS-PAGE indicated complete conversion of the glycoprotein to a form containing a single GlcNAc residue. The modified ribonuclease B was desalted on a Bio-Gel P6DG column and the ribonuclease fractions were freeze-dried.

Step 2. Galactosylation of Endo H-treated ribonuclease B.

Figure 10:
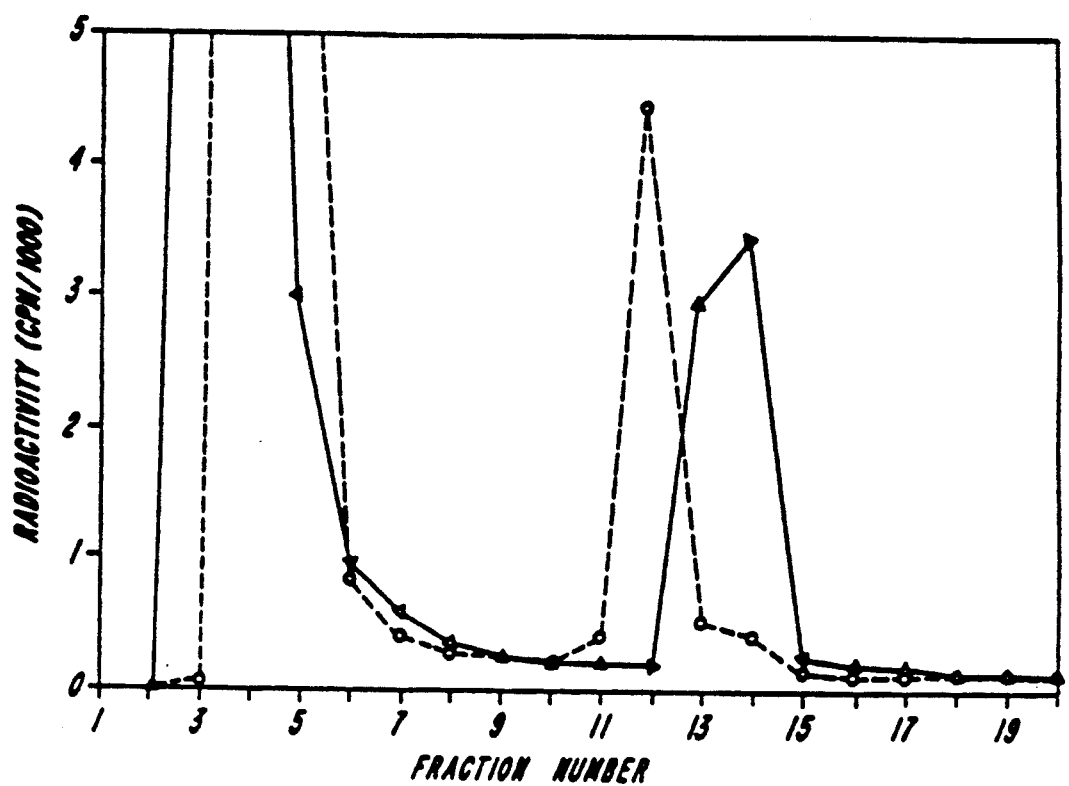
FIG. 10 Analysis of [$^3$H]Gal→GlcNAc-RNase by fast protein liquid chromatography (FPLC) on a Mono S column before (——) and after (Δ———Δ) sialylation with CMP-NeuAc and rat liver α2→6 sialyltransferase, where the column was eluted. with a linear gradient as described below.

Endo H-treated ribonuclease B (400 mg) was incubated for 3 hours at 37° in 250 pl of 0.1M MES, pH 6.3, containing 0.1% Triton X-100, 0.01M MnCl$_2$, 100 mU bovine milk UDP-Gal:GlcNAc-R β1→4 galactosyltransferase and 300 nmol UDP-[$^3$H]Gal (specific activity 17.3 Ci/mol). The galactosylated ribonuclease was analyzed by FPLC on a Mono S column. A linear gradient from 20 mM sodium phosphate, pH 7.95 to 20 mM sodium phosphate containing 1M NaCl was run. The galactosylated ribonuclease eluted at a NaCl concentration of 0.13M. The protein peak measured by UV absorbance (A$_{280}$) coincided with a peak of radioactivity, as shown in FIG. 10 (——). The protein peak eluting at 0.13M NaCl was collected and analyzed by SDS-PAGE. The only protein band detected after staining with Coomassie blue co-migrated with Endo H-treated ribonuclease B (not shown).

Step 3. Sialylation of galactosylated ribonuclease.

A 40 μl aliquot of the reaction mixture from Step 2 was mixed with 10 μl of 6.5 mM CMP-NeuAc and 10 μl of rat liver CMP-NeuAc:Gal-R α2→6 sialyltransferase (1.6 mU, obtained from Genzyme Corp., Boston Mass.) and incubated at 37° C. for 18 hours. The sialylated ribonuclease was analyzed by FPLC on a Mono S column using the conditions described in Step 2. The sialylated ribonuclease eluted at a NaCl concentration of 0.18M, as judged by the profiles of both A$_{280}$ and radioactivity. The profile of radioactivity is shown in FIG. 10, (Δ—Δ). The conversion of Gal→GlcNAc-RNAse to SA→Gal→RNAse appeared to be quantitative.

Although this invention has been described with reference to specific embodiments, it is understood that modifications and variations of the methods for modifying or glycosylating proteins, and the glycosylated proteins, may occur to those skilled in the art. It is intended that all such modifications and variations be included within the scope of the appended claims.

We claim:

1. A method for modifying proteins comprising: the step wherein when the protein contains carbohydrate, removing all carbohydrate exterior to the two innermost GlcNAc residues from the protein to be modified prior to derivatizing the amino acids, reacting the free amino groups of one or more lysines or the amino terminal amino acid or the thiol groups of one or more free cysteines on the protein with a glycoside or thioglycoside represented by the formula S-X, wherein S is a first saccharide or disaccharide selected from the group consisting of N-acetylglucosamine, N-acetyllactosamine and galactose and X is an aglycone, and enzymatically attaching to S one or more additional saccharides selected from the group consisting of galactose, fucose, and sialic acid.

2. The method of claim 1 wherein said aglycone comprises a free amino group or an electrophilic group selected from the group consisting of a carboxylic chloride, carboxylic acid N-hydroxy ester, carboxylic acid azide, an isocyanate, a thioacetate, an alpha halocarbonyl compound, an αβ-unsaturated carbonyl compound, an acyl imidizole and a diazo grouping.

3. The method of claim 1 comprising reacting a glycoside or thioglycoside having an aglycone containing an electrophilic site with an amino acid of the protein selected from the group consisting of cysteine and other amino acids containing free sulfhydryl groups.

4. The method of claim 2 comprising reacting a glycoside or thioglycoside having an aglycone containing a free amino group with glutamine using a transglutaminase.

5. The method of claim 1, wherein the first saccharide is GlcNAc, and wherein said enzymatic attachment comprises:

attaching a galactose residue to the N-acetylglucosamine to form a Gal-GlcNAc→ sequence; and attaching a sialic acid residue to the galactose to form a Sa-Gal-GlcNAc→ sequence.

6. The method of claim 1, wherein the first saccharide is galactose, and wherein said enzymatic attachment comprises:

attaching a sialic acid residue to the galactose to form a Sa-Gal sequence.

7. The method of claim 5 wherein the galactose residue is attached to the N-acetylglucosamine residue by a galactosyltransferase.

8. The method of claim 7 wherein the galactosyltransferase is selected from the group consisting of UDP-Gal:GlcNAc-R β1→4 galactosyltransferase and UDP-Gal:GlcNAc-R β1→3 galactosyltransferase.

9. The method of claim 5 further comprising enzymatically attaching fucose to a Gal→GlcNAc→ sequence.

10. The method of claim 9 wherein the fucose is attached to the Gal-GlcNAc→ sequence with GDP-Fuc:GlcNAc α1→3 fucosyltransferase.

11. The method of claim 5 further comprising attaching the galactose residues to the N-acetylglucosamine in a solution containing a compound selected from the group consisting of a non-ionic detergent, a chaotropic agent, an organic solvent, urea, a protease inhibitor, an exoglycosidase inhibitor, a disulfide bond reducing agent, or a combination thereof.

12. The method of claim 5 wherein the sialic acid residue is attached to the Gal-GlcNAc sequence in an α linkage by a sialyltransferase.

13. The method of claim 12 wherein the sialyltransferase is selected from the group consisting of CMP-SA:-Galβ1→4GlcNAc-R β2→6 sialyltransferase, CMP-SA:Galβ1→3(4)GlcNAc α2→3 sialyltransferase, and CMP-SA:Galβ1→4GlcNAc β2→3 sialyltransferase.

* * * * *